(12) United States Patent
Dee et al.

(10) Patent No.: US 7,788,982 B2
(45) Date of Patent: Sep. 7, 2010

(54) METHOD AND APPARATUS FOR TESTING SHAFTS

(75) Inventors: Alex T. Dee, Carlsbad, CA (US); Zhichen Xi, San Diego, CA (US); Mark Chamberlain, San Diego, CA (US)

(73) Assignee: Fujikura Composite America, Inc., Vista, CA (US)

(*) Notice: Subject to any disclaimer, the term of this patent is extended or adjusted under 35 U.S.C. 154(b) by 63 days.

(21) Appl. No.: 12/110,243

(22) Filed: Apr. 25, 2008

(65) Prior Publication Data
US 2008/0264179 A1 Oct. 30, 2008

Related U.S. Application Data

(60) Provisional application No. 60/914,015, filed on Apr. 25, 2007.

(51) Int. Cl.
*G01N 3/20* (2006.01)
(52) U.S. Cl. .................................... 73/851; 73/760
(58) Field of Classification Search ............ 73/65.03, 73/851, 760
See application file for complete search history.

(56) References Cited

U.S. PATENT DOCUMENTS

| | | | |
|---|---|---|---|
| 3,196,669 A | 7/1965 | Fischer | |
| 3,589,175 A | 6/1971 | Bock | |
| 4,003,247 A | 1/1977 | Moser et al. | |
| 4,051,616 A * | 10/1977 | Mathauser | 43/17 |
| 4,283,957 A | 8/1981 | Zobrist et al. | |
| 4,488,444 A * | 12/1984 | Weidmann et al. | 73/862.452 |
| 4,603,577 A * | 8/1986 | Johnson et al. | 73/65.03 |
| 4,864,863 A | 9/1989 | Yarm | |
| 5,285,680 A * | 2/1994 | Sun | 73/65.03 |
| 5,438,262 A | 8/1995 | Nanjyo et al. | |
| 5,448,917 A | 9/1995 | Maciejewski | |
| 5,503,024 A * | 4/1996 | Bechtel et al. | 73/852 |

(Continued)

FOREIGN PATENT DOCUMENTS

JP 07-231953 A 9/1995

OTHER PUBLICATIONS

PCT; App. No. PCT/US08/061685; International Search Report; mailed Oct. 17, 2008.

(Continued)

*Primary Examiner*—Max Noori
(74) *Attorney, Agent, or Firm*—Fitch Even Tabin & Flannery

(57) ABSTRACT

Methods and apparatus are provided for testing shafts, such as golf club shafts. In one embodiment, the invention can be characterized as a shaft tester comprising: a frame; a first shaft support supporting a first portion of a shaft at a first fixed position; a second shaft support supporting a second portion of the shaft at a second fixed position; and a third shaft support supporting a third portion of the shaft at a third fixed position. An actuator couples to the third shaft support to displace the third portion relative to the first and second portions to deflect the shaft. A sensor couples to one of the first, second and third supports outputting a signal corresponding to a force exerted by the shaft due. A controller controls displacement of the shaft. In some embodiments, the shaft is rotated while being deflected.

30 Claims, 14 Drawing Sheets

U.S. PATENT DOCUMENTS

| | | | |
|---|---|---|---|
| 5,606,134 A * | 2/1997 | Stieber | 73/849 |
| 5,731,524 A | 3/1998 | Matsumoto et al. | |
| 5,773,714 A * | 6/1998 | Shead | 73/105 |
| 5,814,773 A * | 9/1998 | Latiri | 177/171 |
| 5,872,318 A | 2/1999 | Troffer et al. | |
| 6,250,168 B1 * | 6/2001 | D'Aguanno | 73/865.3 |
| 6,405,595 B1 | 6/2002 | Harrison | |
| 6,765,156 B2 * | 7/2004 | Latiri | 177/171 |
| 6,918,306 B1 * | 7/2005 | Cavallaro et al. | 73/849 |
| 7,021,096 B2 * | 4/2006 | Barnett | 72/31.1 |
| 7,080,565 B2 | 7/2006 | Delair et al. | |
| 7,204,152 B2 | 4/2007 | Woodward | |
| 2002/0083772 A1 | 7/2002 | Sonnichsen | |

OTHER PUBLICATIONS

PCT; App. No. PCT/US08/061685; Written Opinion of the International Searching Authority mailed Oct. 17, 2008.

* cited by examiner

METHOD AND APPARATUS FOR TESTING SHAFTS

This application claims the benefit of U.S. Provisional Application No. 60/914,015, filed Apr. 25, 2007, which is incorporated in its entirety herein by reference.

BACKGROUND OF THE INVENTION

1. Field of the Invention

The present invention relates generally to the testing shafts, and more specifically to testing of golf club shafts.

2. Discussion of the Related Art

Currently there are a variety of devices to test the durability of a shaft. Different tests have been designed and developed to filter out shafts that don't have acceptable structural strength. For example, in the golf industry, a commonly used shaft destruction test is the air cannon test, whereby a ball is shot at a golf head at a specified speed until an acceptable impact quantity is reached or there is a catastrophic break (the head is bonded to the shaft as would be in the field). This test requires multiple iterations (often times up to 3000 hits and beyond). Additionally, air cannon tests are time consuming, noisy, require human supervision and are potentially dangerous (essentially since a projectile is launched at high speed toward the club head).

The above-described methods test the structural integrity of a composite golf shaft. At least one problem with these methods and other composite golf shaft testing methods is that all of these tests focus on one singular location or point on the shaft and not at different points of the or the entire circumference. This type of testing can lead to a "false positive" destructive test result. One reason for a "false positive" result is because of composite ply drop offs. Variations in shaft wall thickness caused by ply drop-offs or poor designs can lead to strength variations in the shaft about its circumference.

SUMMARY OF THE INVENTION

Several embodiments of the invention provide methods and apparatus for testing shafts, such as golf club shafts. In one embodiment, the invention can be characterized as a shaft tester comprising: a frame; a first shaft support coupled to the frame, the first shaft support adapted to support a first portion of a shaft at a first fixed position; a second shaft support coupled to the frame, the second shaft support adapted to support a second portion of the shaft at a second fixed position; and a third shaft support coupled to the frame, the third shaft support adapted to support a third portion of the shaft at a third fixed position. The shaft tester also comprises an actuator coupled to the third shaft support and adapted to displace the third portion relative to the first portion and the second portion to cause a deflection in the shaft; a sensor coupled to one of the first support, the second support and the third support and adapted to output a signal corresponding to a load force exerted by the shaft due to the deflection; and a controller coupled to the actuator and adapted to control displacement of the shaft.

In another embodiment, the invention can be characterized as a shaft tester comprising: a frame; a first shaft support coupled to the frame, the first shaft support adapted to support a first portion of a shaft at a first fixed position; and a second shaft support coupled to the frame, the second shaft support adapted to support a second portion of the shaft at a second fixed position. The tester also includes an actuator coupled to the second shaft support and adapted to displace the second portion relative to the first portion to cause a lateral deflection in the shaft; a sensor coupled to one of the first support, the second support and the third support and adapted to output a signal corresponding to a load force exerted by the shaft due to the lateral deflection; a motor adapted to rotate the shaft when the shaft experiences the lateral deflection; and a controller coupled to the actuator and the motor and adapted to control the deflection and rotation.

In a further embodiment, the invention may be characterized as a method for use in testing a shaft comprising the steps: supporting a first portion of a shaft at a first fixed position; supporting a second portion of a shaft at a second fixed position; supporting a third portion of a shaft at a third fixed position; displacing the third portion relative to the first portion and the second portion causing a deflection in the shaft; outputting a signal corresponding to a load force exerted by the shaft due to the displacing; and controlling a displacement of the shaft.

In another embodiment, the invention may be characterized as a method for use in testing a shaft comprising the steps of: supporting a first portion of a shaft at a first fixed position; supporting a second portion of a shaft at a second fixed position; laterally displacing the second portion relative to the first portion and the second portion causing a lateral deflection in the shaft; outputting a signal corresponding to a load force exerted by the shaft due to the displacing; rotating the shaft during the displacing step; and controlling the displacing and the rotating of the shaft.

In yet another embodiment, the invention may be characterized as a method for use in testing a shaft comprising the steps: displacing a first portion of a shaft relative to a second portion of the shaft to cause a deflection in the shaft; rotating the shaft when the shaft is experiencing the deflection; measuring a load force exerted by the shaft due to the deflection during the rotation; monitoring the measured load force over time; and generating a fatigue profile of the shaft based at least in part on the monitoring step.

In a further embodiment, the invention may be characterized as a method for use in testing a shaft comprising the steps: displacing a first portion of a first shaft relative to a second portion of the first shaft to cause a deflection in the first shaft causing a load force at a first level to be exerted by the first shaft; rotating the first shaft when the first shaft is experiencing the deflection until the first shaft fails; determining a first length of time until the first shaft failed; displacing a first portion of a second shaft relative to a second portion of the second shaft to cause a deflection in the second shaft causing a load force at a second level to be exerted by the second shaft; rotating the second shaft when the second shaft is experiencing the deflection until the second shaft fails; determining a second length of time until the second shaft failed; and generating a fatigue life profile based at least in part on testing the first shaft and the second to extrapolate a fatigue life of additional shafts not tested.

BRIEF DESCRIPTION OF THE DRAWINGS

The above and other aspects, features and advantages of several embodiments of the present invention will be more apparent from the following more particular description thereof, presented in conjunction with the following drawings.

Figure 1:
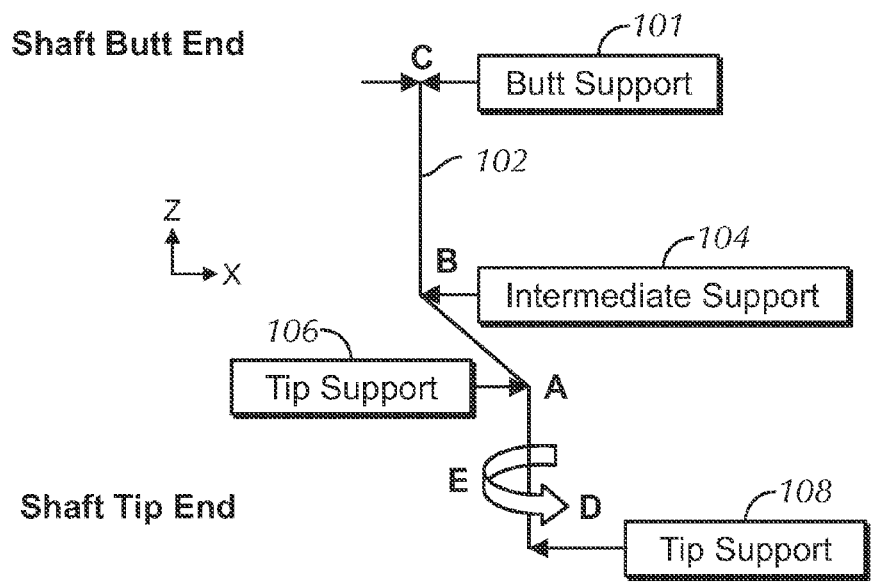
FIG. 1 is one embodiment of a free body diagram of a shaft testing device in accordance with several embodiments of the invention.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention.

DETAILED DESCRIPTION

The following description is not to be taken in a limiting sense, but is made merely for the purpose of describing the general principles of exemplary embodiments. The scope of the invention should be determined with reference to the claims.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Several embodiments of the present invention addresses the problems described above. In several embodiments, a shaft testing device or machine and related methods are provided to test the characteristics of a shaft or similar elongate structure that is intended to deflect or to bend in use. For example, a shaft is deflected to determine the breaking point of the shaft. In other embodiments, the shaft is deflected about various rotational locations of the shaft. In some embodiments, the shaft is deflected while being rotated to test for breakage or to generate a profile of the fatigue or fatigue life of the shaft. Generally, in some embodiments, when testing the fatigue life of a shaft, the shaft is maintained in a deflected state while being rotated over time while measuring load forces exerted by the shaft at one or more points of the shaft and/or calculating moments generated at one or more locations of the shaft. This data may be analyzed over time and a profile can be generated of the fatigue life of the shaft, for example, the ability of the shaft to withstand intended deflection at various circumferential locations over time. In some embodiments, the testers and methods provided are safe and quiet to use, can be performed quickly, and can be used in an automated fashion without human supervision. Several embodiments are also safe in that they are not ballistics tests.

In some embodiments, a shaft testing device tests shaft fatigue at up to 360 degrees of a golf shaft, whereby full cycles of tensile and compressive loads are applied to the shaft. This gives a better understanding of the shaft's structural integrity at multiple locations of the circumference to throughout the entire circumference of the shaft without having to worry about how the shaft is oriented during testing. Furthermore, in some embodiments, the system tests the bending fatigue of a shaft without a golf head, or any reasonable facsimile, attached or bonded to the shaft.

Referring to FIG. 1, a free body diagram of a shaft testing device is shown in accordance with some embodiments of the present invention. FIG. 1 depicts loads on a shaft 102 under test, for example, the loads apply a moment at the tip end that mimic the moment on a shaft during a golf swing when the shaft 102 is deflected between two portions, the moment results in a deflection shape that mimics the deflection shape occurring during an actual golf swing. The shaft 102 is clamped by a butt support 101 at a butt end (illustrated at point C), with an intermediate support 104 at point B and two tip supports 106, 108, the tip supports 106, 108 mimicking a shaft location in a golf head. That is, in some embodiments, the tip support 106 is intended to be located at the location at the point where the shaft first enters a hosel or club head. The tip support 106 is illustrated at point A and the tip support 108 is illustrated at point D. In one embodiment, the tip supports 106 and 108 are located approximately two inches apart from one another (along the z axis), with the tip support 106 absorbing the majority of the load at the tip when the shaft tip end is displaced relative to the shaft butt end. For example, in the illustrated embodiment, the shaft tip end is laterally or linearly displaced along the x axis relative to the butt end of the shaft, such that the shaft is deflected about the intermediate support 104. The intermediate support 104 is adjustable in a vertical direction (e.g., z axis) in order to accommodate different types of shafts at different lengths and varying loading conditions. As depicted by the arrow E around the shaft tip end, in some embodiments, the shaft testing machine rotates the shaft 102 while the shaft is in the bent or deflected (loaded) position illustrated. In some embodiments, the intermediate support 104 is located toward the shaft tip end of the shaft 102 in order to focus the majority of the bending stress toward the tip end of the shaft (i.e., the portion of the shaft that experiences the majority of the bending stresses in actual use in a golf club). Thus, in one form, the intermediate support 104 is located less than 50% of the length of the shaft toward the tip end, in another form, less than 40% of the length of the shaft toward the tip end, while in another form, less than 30% of the length of the shaft toward the tip end.

The supports 101, 104, 106 and 108 rigidly fix the shaft in an x, y, z space but allow the shaft to rotate about the z axis. Furthermore, in the illustrated embodiment, as will be made more clear in the following discussion, the tip supports 106 and 108 are movable about the x axis to laterally displace or deflect the tip end of the shaft relative to the butt end of the shaft and the portion of the shaft contacting the intermediate support 104. In some embodiments, the tip end of the shaft 102 is rigidly fixed to a sleeve which is held in position by the tip supports 106, 108.

Figure 2:
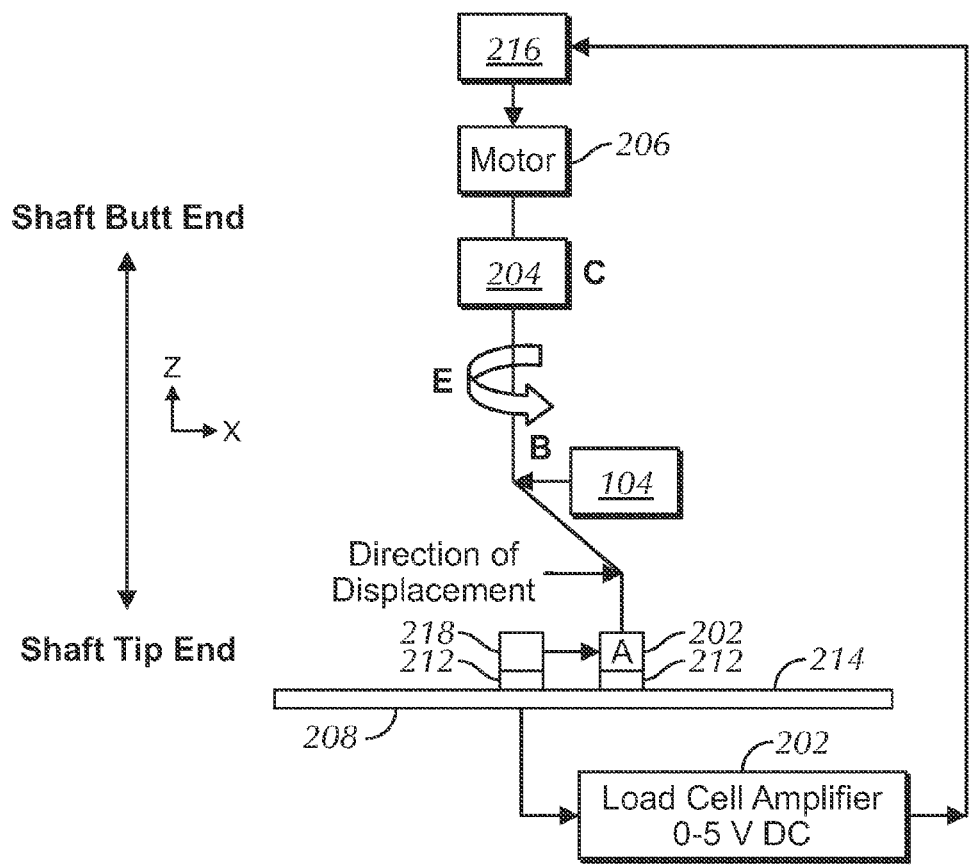
FIG. 2 is a schematic diagram of a control loop of a shaft testing device in accordance with some embodiments.

Referring to FIG. 2, a basic schematic of a control loop of a shaft testing device 200 is shown in accordance with one embodiment of the present invention.

In operation, the tip of the shaft 102 is loaded into a bearing block 202 (which implements tip supports 106 and 108) while the butt end of the shaft is inserted into a chuck 204 (implementing the butt support 101 and coupled to part of a rotary motor 206) and then manually tightened. The chuck 204 holds one portion (in this case, the butt end) of the shaft in a fixed x, y, z position and also holds the shaft so that it can not rotate within the chuck 204. A bearing platform 208 supporting the bearing block 202 is then raised or lowered along the z axis in order to make the top of the bearing block 202 flush with what would be the top of the hosel in a golf club. That is, the portion of the shaft at the top of the bearing block 202 should be the location of the shaft that would be where the shaft enters the hosel (i.e., the bearing block 202 mimics the hosel or club head). In other words, the system mimics the shaft/club system that is seen in the field. The height of the bearing platform 208 may be adjusted within the frame, e.g., the bearing platform 208 is slidingly coupled to the frame. The shaft 102 is then horizontally or laterally displaced, e.g., about the x axis in the illustrated embodiment, according to either a target distance or load relative to the shaft butt end. To displace the shaft tip end, the bearing block 202 is attached to a linear bearing guide 212 that is horizontally or laterally displaced along a stationary linear guide rail 214. Thus, the tip end of the shaft is linearly displaced relative to the stationary butt end at the chuck 204/motor 206. In some embodiments, the bearing block 202 is manually displaced. In some embodiments, the bearing block 202 displacement is automated; that is, the bearing block is moved along the linear guide rail 214 in response to a command from a controller 216. In some embodiments, a brake (not shown in FIG. 2) locks the block into place. A load cell 218 is coupled to the bearing block 202 (via a load cell coupling) to measure the load or force applied to the bearing block 202 by the shaft due to the deflection. The load cell 218 outputs an electrical signal that is amplified (e.g., by amplifier 220) and input to the controller 216 and/or computer, the electrical signal corresponding to the force or load. As it is used throughout this specification, the term load cell may generically be referred to as a sensor.

Once deflected, while being maintained in the deflected state, the shaft 102 is caused to rotate by the motor 206 under control of the controller 216. In some embodiments, a user inputs a target frequency at which the shaft rotates under test. In some embodiments, a user inputs a threshold/trip point that allows the device or machine to automatically stop when the load drops below the prescribed threshold. For example, if the shaft were to fail (break), the measured load (from the load cell 218) would drop below the threshold, and the rotary motor 206 would be disabled to stop rotation. Thus, in one form, the output of the load cell 218 is used by the controller 216 controlling the operation of the rotary motor 206. In some embodiments a user initiates testing (shaft rotation) by interacting with the human machine interface. In some embodiments, a user initiates testing by interacting with a PC coupled to the system (i.e., the controller includes or is coupled to a personal computer). In some embodiments, the system runs until manually terminated. In alternative embodiments, the system is automatically terminated when failure occurs (a shaft breaks) or a stopping event occurs. A stopping event is, for example, an elapse of a user-selected amount of time, a change in load, or other event in response to which the testing will terminate.

While the shaft testing machine 200 is running (i.e., the shaft is deflected and rotated), the load measurements and corresponding rotary location measurements or readings are output to the controller 216 to be processed (or further output to a computer). In some embodiments, the motor 206 includes a rotary encoder in order to determine (and output) its circumferential location at all points in time. Load cell measurements are correlated to circumferential positions to output, display, and/or process load measurements at multiple or all circumferential locations about the shaft, depending on the resolution of the rotary encoder. In some embodiments, the user can program the frequency at which to record and/or display load measurements and also program the number of locations about the circumference to record and/or display the load measurements.

Figure 3:
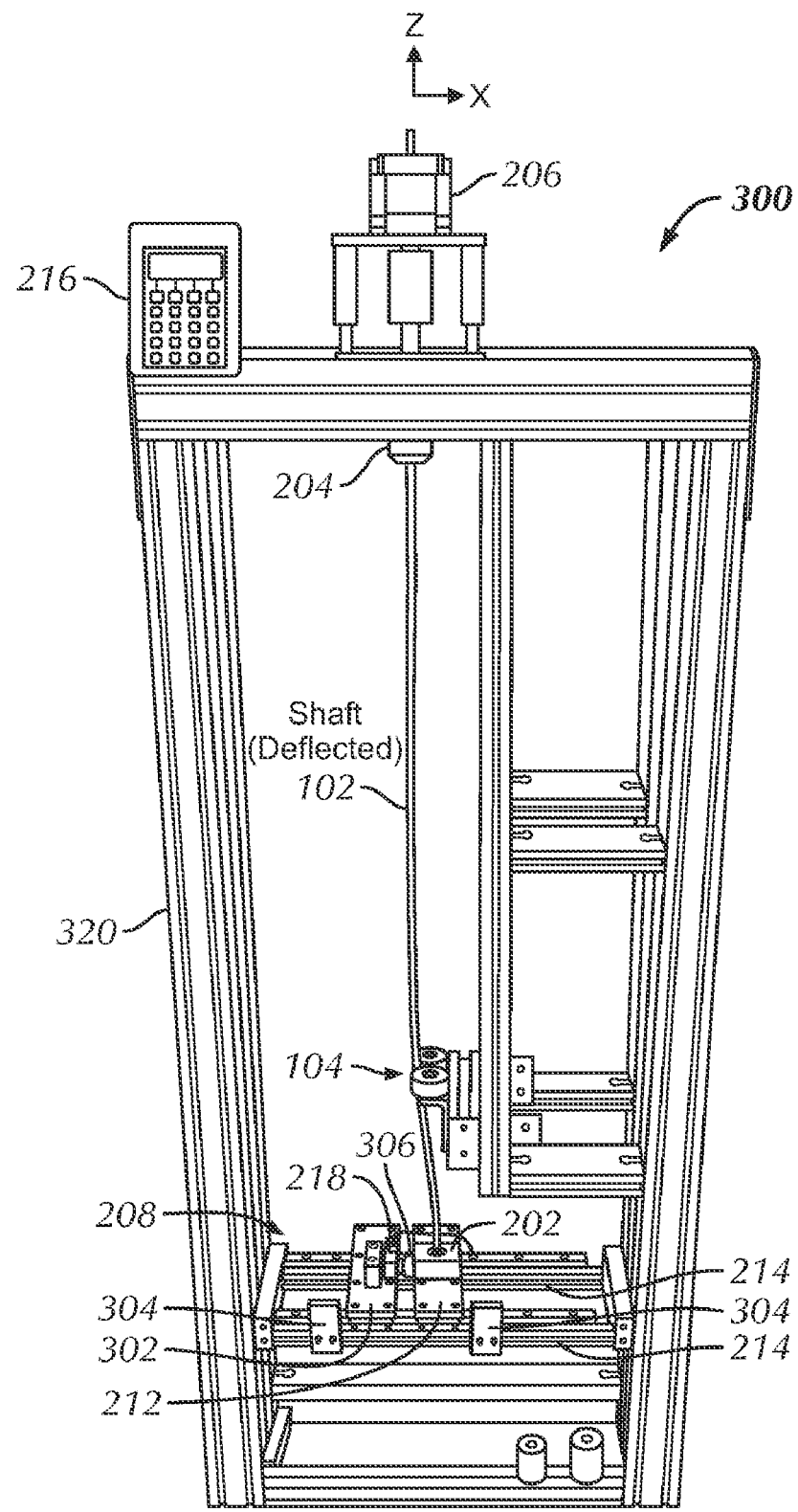
FIG. 3 is a shaft testing device in accordance with several embodiments of the invention.
Figure 4:
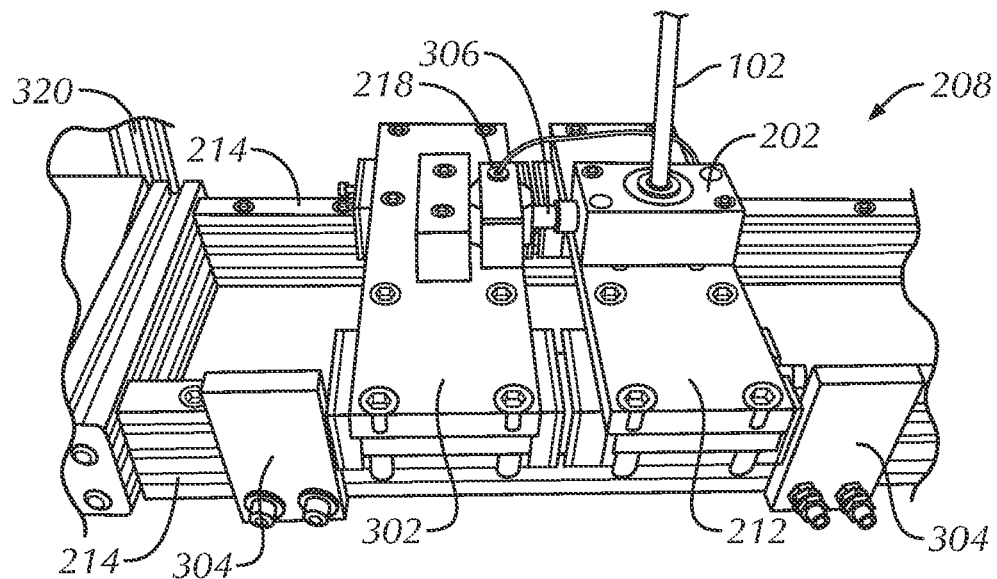
FIG. 4 is a perspective view of the bearing platform of the shaft testing device of FIG. 3 according to several embodiments.
Figure 5:
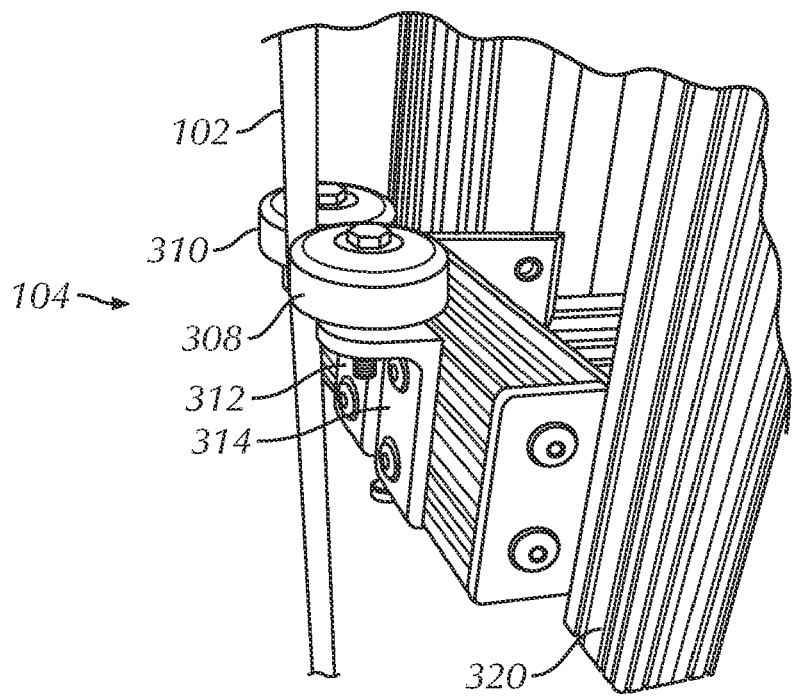
FIG. 5 is a perspective view of the intermediate support of the shaft testing device of FIG. 3 according to several embodiments.

Reference is now made to FIGS. 3-5. FIG. 3 illustrates a shaft testing device 300 in accordance with several embodiments of the invention. FIG. 4 illustrates the bearing platform and FIG. 5 illustrates the intermediate support of the shaft testing device of FIG. 3 according to several embodiments. The shaft testing device operates generally according to the description of FIGS. 1-2 and is presented to provide an example of and further description of a shaft testing device or machine according to several embodiments.

The shaft testing device 300 for testing the shaft 102 includes a frame 320, the chuck 204, the motor 206 and the bearing platform 208 including the bearing block 202, the linear bearing guide 212, the load cell 218, a load cell bearing guide 302, linear guide rails 214, stoppers 304, and a load cell coupling 306. The device 300 also includes the intermediary support 104 including wheels 308, 310 and support brackets 312, 314 rigidly mounted to the frame 320. The device 300 also includes the controller 216, which in the illustrated embodiment has a human interface. Embodiments of several of the components of FIGS. 3-5 are described below.

The motor 206 is coupled to the chuck 204 and causes rotation of the shaft 102 about the z axis under deflection. In some embodiments, the system uses a NEMA 34 single stack stepper motor. In one embodiment, the motor 206 rotates the chuck 204 that holds the butt end of the shaft, thus rotating the entire shaft. The motor 206 controls partial and/or full rotations. The motor 206 also has the capability to be easily manipulated using the controller 216 and can run for extended periods of time under nominal loads.

In some embodiments, the feedback loop is a closed system defined by the controller 216, the motor 206, the load cell 218 and the load cell amplifier 220. In some embodiments, the controller 216 includes a Human Machine Interface (HMI), whereas in other embodiments, the controller is coupled to a computer running software that allows a human to program and control the controller. Under test, in one embodiment, the tip end of the shaft is manually displaced relative to another portion of the shaft (e.g., along the x axis), which puts a load on the shaft at points A, B and C (see FIGS. 1 and 2). The peak load is typically located at Point A.

In some embodiments, the load at point A is measured by the load cell 218 (as a load exerted by the bearing block 202 on the load cell 218), amplified to 0-5V DC and sent to the controller 216. The controller 216 receives a signal from the load cell amplifier 220 within the prescribed 0-5V analog input range. This information is converted into binary units, which in turn is calibrated into a load (lbs). The binary units are directly proportional to the capacity of the load cell 218. In some embodiments, for example, the capacity of the load cell is 500 lbs. In FIG. 3, the controller 216 is illustrated as a small input device with input keys and a display, and including a controller or programmable logic controller (PLC) for recording, processing and/or outputting load and angular position measurements to a computer.

In the event of shaft breakage the controller 216 is programmed to stop the motor 206 when the load goes below a certain prescribed threshold.

As illustrated in FIGS. 1 and 2, the shaft testing device 300 provides three boundary points at A, B and C. Point A is defined at the bearing block 202. In the embodiment illustrated in FIG. 2, the bearing block 202 holds the tip end of the shaft. The shaft threads or fits through the bearing block and the bearing block is laterally displaced (e.g., along the x axis) relative to the butt end of the shaft (thus, bending the shaft). In preferred form, as illustrated, the shaft is bent about point B at the intermediate support 104 to place the majority of the bending stress on the tip end of the shaft. When testing is initiated, the shaft is caused to rotate within the bearing block 202. That is, in some embodiments, the portion of the bearing block 202 that contacts the shaft is rotatable within the bearing block. In one embodiment, the bearing block 202 contains two bearings stacked 2 inches apart in a block of Aluminum. It is noted that the bearing block may be generically referred to as a holder or a support that holds or supports a portion (e.g., the tip end) of the shaft in a fixed position (e.g., fixed but adjustable x-y-z locational position while allowing rotation of the shaft about the z axis). It is understand that this support or holder may be located at the tip end of the shaft or at another portion of the shaft.

In embodiments employing an intermediate support 104, point B is defined by the intermediate support. The intermediate support 104 is adjustable in a vertical direction along the z axis (e.g., along a portion of the frame) in order to accommodate different types of shafts at different lengths and to simulate varying loading conditions depending on the characteristics to be tested. Generally, the intermediate support 104 provides a rigid lateral support of the shaft while allowing the shaft to rotate. In some embodiments, low friction wheels 308 and 310 are coupled to a frame (via one or more supports or brackets 312 and 314) and are used as the intermediate support. One of ordinary skill in the art will recognize that there are numerous low friction rotary devices that can support a shaft while allowing it to rotate and minimize contact friction between the shaft and the wheel. In some embodiments, depending on the application of the shaft being tested, no intermediate support is provided. However, in many applications of testing a golf shaft, it is desired to focus the bending forces toward the tip end of the shaft; thus, the intermediate support 104 is provided. In some embodiments, the intermediate support 104 is not used; however, further deflection (lateral displacement of the shaft and tip ends) is needed to achieve the same deflection or load. It is noted that the intermediate support 104 may be generically referred to as a holder or a support that holds or supports a portion (e.g., an intermediary portion in between the tip and butt ends) of the shaft in a fixed position (e.g., fixed x-y-z locational position while allowing rotation of the shaft about the z axis).

Point C is defined in some embodiments by the chuck 204. In the illustrated embodiment, the chuck 204 holds one portion of the shaft (e.g., the butt end) in a fixed location, but causes rotation of the shaft. In some embodiments, the chuck 204 is a standard drill press chuck that opens up to accept a 0.620" butt end of a golf shaft. In some embodiments, it also has a threaded end, as opposed to an arbor on a lathe chuck. It is noted that the chuck may be generically referred to as a holder or support that holds or supports a portion (e.g., the butt end) of the shaft in a fixed position (e.g., fixed x-y-z locational position and fixed but adjustable rotational position).

The frame 320 rigidly couples the various components together and maintains the various components at a fixed orientation. In some embodiments, the frame 320 is made of extruded aluminum for its structural members. The extruded aluminum material has advantages to that of a conventional welded steel frame in weight, cost and overall modularity. In some embodiments, a multitude of attachments and fasteners are coupled to the extruded aluminum frame. Generally, the frame provides a structure to rigidly hold to which supports points A, B, C relative to each other. It is understand that the frame may comprise one or more frames or one or more frame members or other structure to maintain points A, B, C in a fixed (although adjustable) relationship with each other.

In the embodiment of FIGS. 3-5, the chuck 204 rigidly holds or supports the butt end of the shaft in an x-y-z position and in a rotary position, the bearing block 202 rigidly holds or supports the tip end of the shaft in an x-y-z position but does not rigidly hold the tip end in a rotary position. In other embodiments, the butt end is rigidly held but allowed to rotate while the tip end is rigidly held in both position and rotation (tip end being coupled to the rotary motor). In other embodiments, both the tip end and the butt end extend into and/or through bearing blocks that rigidly hold the end in positional location, but allow rotation. In this case, one end of the shaft (e.g., extending through a bearing block) is coupled to a rotary motor or another portion of the shaft is coupling to a rotary mechanism, such as a belt drive coupled to a rotary motor.

As shown in FIGS. 3-5, some embodiments of the frame are rectangular such that a shaft is disposed vertically within the frame. The intermediate support 104 is coupled to a vertical aluminum column situated inside the frame, the vertical aluminum column coupled to the frame by aluminum arms.

In some embodiments, linear ball bearings are used to displace the bearing block 202, e.g., laterally displace the bearing block 202 relative to the chuck 204). In one example, the return force on Point A is about 115 lbs. This force makes it difficult to manually displace the bearing block 202 along the x axis with a shaft inserted. There is also a large moment/torque that is created (a moment is defined as a force over a distance) upon displacement. This force literally wants to "peel" the bearing block 202, as well as the linear bearing guides 212 and 218 off of the rails 214. Because of this, the linear bearing guides 212, 218 have a robust static/dynamic load capability in some embodiments. In some embodiments, the load capability of the linear bearing guides is 55 kN. As illustrated in the example implementation of FIGS. 3-4), the bearing block 202 and the load cell 218 are mounted and move together along two linear guide rails 214. Once in the proper position to cause the desired deflection, the bearing block 202 and the load cell 218 are locked into position on the linear guide rail 214, e.g., using locking brackets or stoppers 304. The load cell 218 is coupled to the bearing block via a load cell coupling 306. In some embodiments, the movement of the bearing block/load cell may be electronically controlled using an electromechanical actuator.

In several embodiments, the load cell 218 is a transducer, which converts force into a measurable electrical output. Although there are many varieties of load cells, strain gage based load cells are the most commonly used type. Strain Gauge load cells convert the load acting on them into electrical signals. The gauges themselves are bonded onto a beam or structural member that deforms when weight is applied. In some embodiments, four strain gages are used to obtain maximum sensitivity and temperature compensation. Two of the gauges are usually in tension, and two in compression, and are wired with compensation adjustments. When weight is applied (the shaft is deflected), the strain changes the electrical resistance of the gauges in proportion to the load.

In some embodiments, a 500 lb capacity load cell is used along with an output amplifier (not shown in FIG. 3). A load cell with this capacity is appropriate because the known load does not exceed 500 lb. The amplifier increases the signal strength to an acceptable level (0-5V DC) so that the controller can read it. The load applied to a shaft is dependent upon many factors including the thickness and strength of the shaft and the amount of displacement.

In some embodiments, there are a plurality of intermediate supports. For example, in some embodiments there is one additional intermediate support than is shown in FIG. 3. The intermediate supports may be positioned to provide a support or force on the shaft in the same or different directions. For example, in embodiments with two intermediate supports, the supports are located on opposite sides of the shaft in different vertical positions from each other and apply a force on the shaft in opposite directions. Both intermediate supports may be adjusted up and down vertically in order to accommodate different types of shafts at different lengths and varying loading conditions. In some embodiments, intermediate supports are supported by aluminum vertical columns supported by aluminum arms coupled to the frame. In some embodiments, a load cell may be coupled to one or more of the intermediate supports to provide additional load measurements at various points of interest along the shaft.

In some embodiments the load cell measures a load at the butt end of the shaft instead of in addition to load measurements taken at or near the tip end. In some embodiments, the butt end of the shaft rotates within a bearing block while the tip end of the shaft is fixedly held by a clamp or chuck. In some embodiments, the motor is located on the bottom of the frame. In some embodiments, the motor rotates a chuck holding the tip end of the shaft.

The fatigue testers described herein may be used with a variety of different shafts, such as sports implements (e.g., golf shafts, pole vault shafts, etc.) or any or shaft that is intended to deflect or bend in use. In some embodiments, the testers and methods described herein are used to test the deflection characteristics of a shaft, for example to test failure (breaking point). In other embodiments, the testers and methods are used to test fatigue life in deflection (e.g., bended). For example, the shaft is loaded (deflected to simulate use) for periods of time. Over time, fatigue characteristics can be generated from load measurements to determine the deflection endurance or fatigue of a shaft, for example, for quality control purposes.

In some embodiments, data from a load cell is sent to a PC (not shown) and a representation of the data displayed. Data relating to the load at a plurality of points around the circumference of the shaft is sent to the PC. Data relating to the number of revolutions of the shaft is sent to the PC. In some embodiments, the moment (force over a distance, i.e. the length of the shaft) is calculated at the PC. In some embodiments fatigue life of a shaft may be predicted based upon data gathered at the PC.

In one embodiment, the invention may be characterized as a method for testing a shaft comprising holding a first portion of a shaft in a first holder; holding a second portion of the shaft in a second holder; and displacing the second portion of the shaft relative to the first portion. In a further variation, the shaft is rotated while being displaced.

In alternative embodiments, a sleeve is bonded to the tip end of the shaft to simulate an actual golf head hosel. Since the shaft tip and hosel are in contact in a shaft in use, the golf head hosel's design can greatly influence shaft life. In this embodiment, the bearing block 202 is configured to receive the sleeve, holding the tip end of the shaft and the sleeve in an x, y, z location, but allowing both the tip end and the sleeve to rotate within the bearing block.

Figure 6:
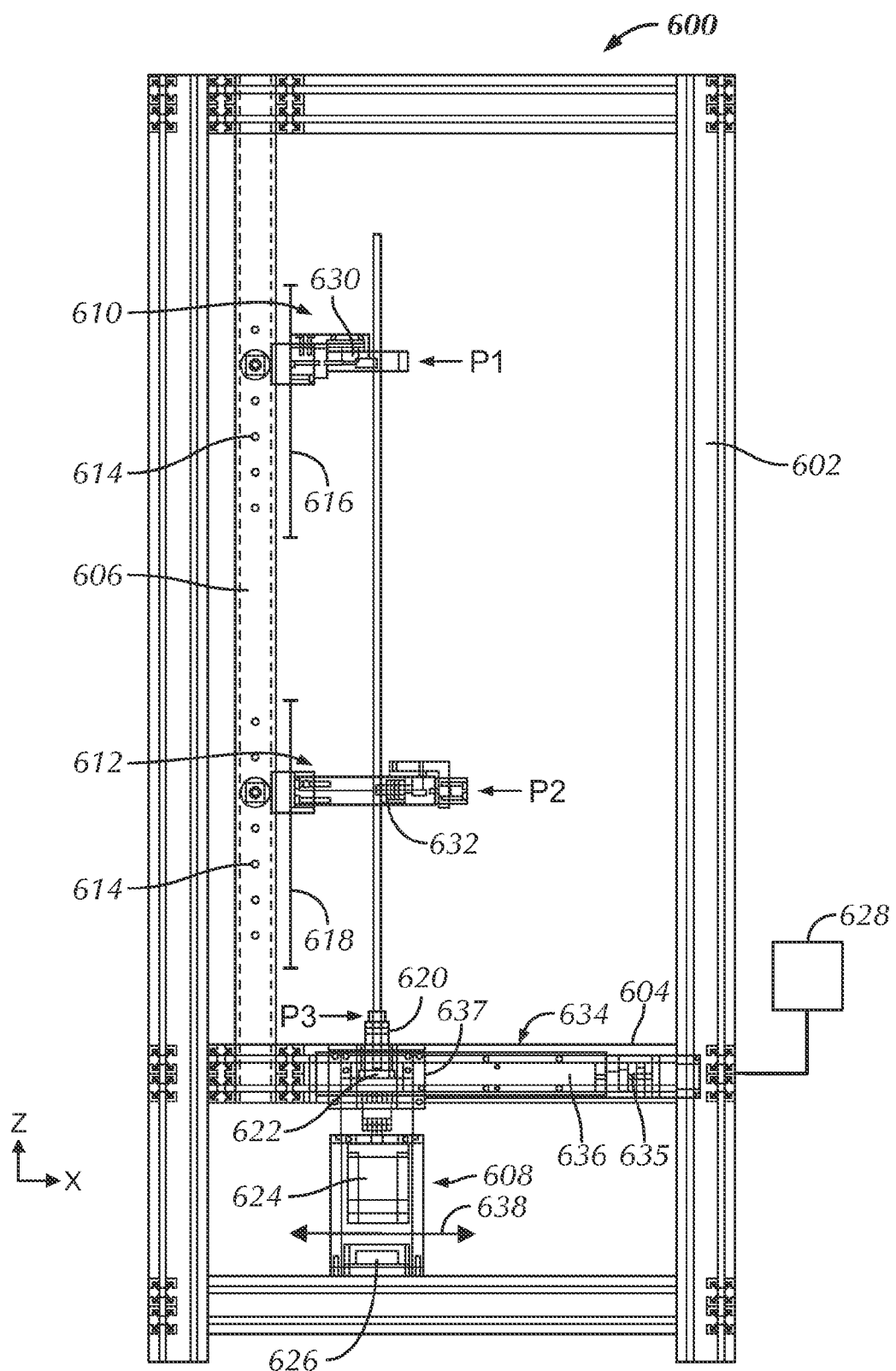
FIG. 6 is a shaft testing device in accordance with several embodiments of the invention.

Referring next to FIG. 6, a shaft testing device 600 is illustrated in accordance with several additional embodiments of the invention. The shaft testing device 600 includes a frame 602 having a base support 604 rigidly fixed within the frame 602 and having a linear guide rail 606 extending upwardly therefrom. The base support 604 includes a motor assembly 608 and electronics. An upper support assembly 610 and a lower support assembly 612 are rigidly coupled to the linear guide rail 606 at different vertical locations. The upper support assembly 610 and the lower support assembly 612 may be adjusted to different heights along the linear guide rail 606 to accommodate different length shafts and to provide for different deflection testing conditions. For example, the linear guide rail 606 may be provided with a series of spaced holes 614 through which a pin lock inserts or through which a stem of a threaded knob inserts to hold the support assembly at a given vertical height. This height may be manually adjusted as needed. For example, as illustrated, the upper support assembly 610 may be positioned with a first vertical range 616 and the lower support assembly 612 may be positioned with a second vertical range 618.

The base support 604 also includes a shaft holder 620 (which may also be referred to as a shaft support). In the illustrated embodiment, the shaft holder 620 receives the tip end of the shaft 102. In preferred form, the tip end of the shaft is bonded within a shaft sleeve that is used to simulate the shaft-hosel interface, preferably using the same bonding agent as would be used between a shaft and a hosel. Accordingly, the shaft holder 620 is configured to receive the sleeve and rigidly hold the sleeve (i.e., portion of the shaft) in a fixed x, y, z and rotation position within the shaft holder 620. In one version, a screw or axle is moved through an opening in the support holder 620 and the sleeve to fixedly engage the tip end of the shaft with the shaft holder 620. The shaft holder is coupled to a motor drive shaft 622 which is rotationally coupled to a rotary motor 624. A cooling fan 626 is used to remove excessive heat generated by the motor 624. The base support also houses various electronics, such as a controller (not specifically illustrated) and rotary and linear actuator components. In this embodiment, the controller does not include a human machine interface, but electrical connections to a computer 628. In one embodiment, the controller is a programmable logic controller (PLC).

Figure 7:
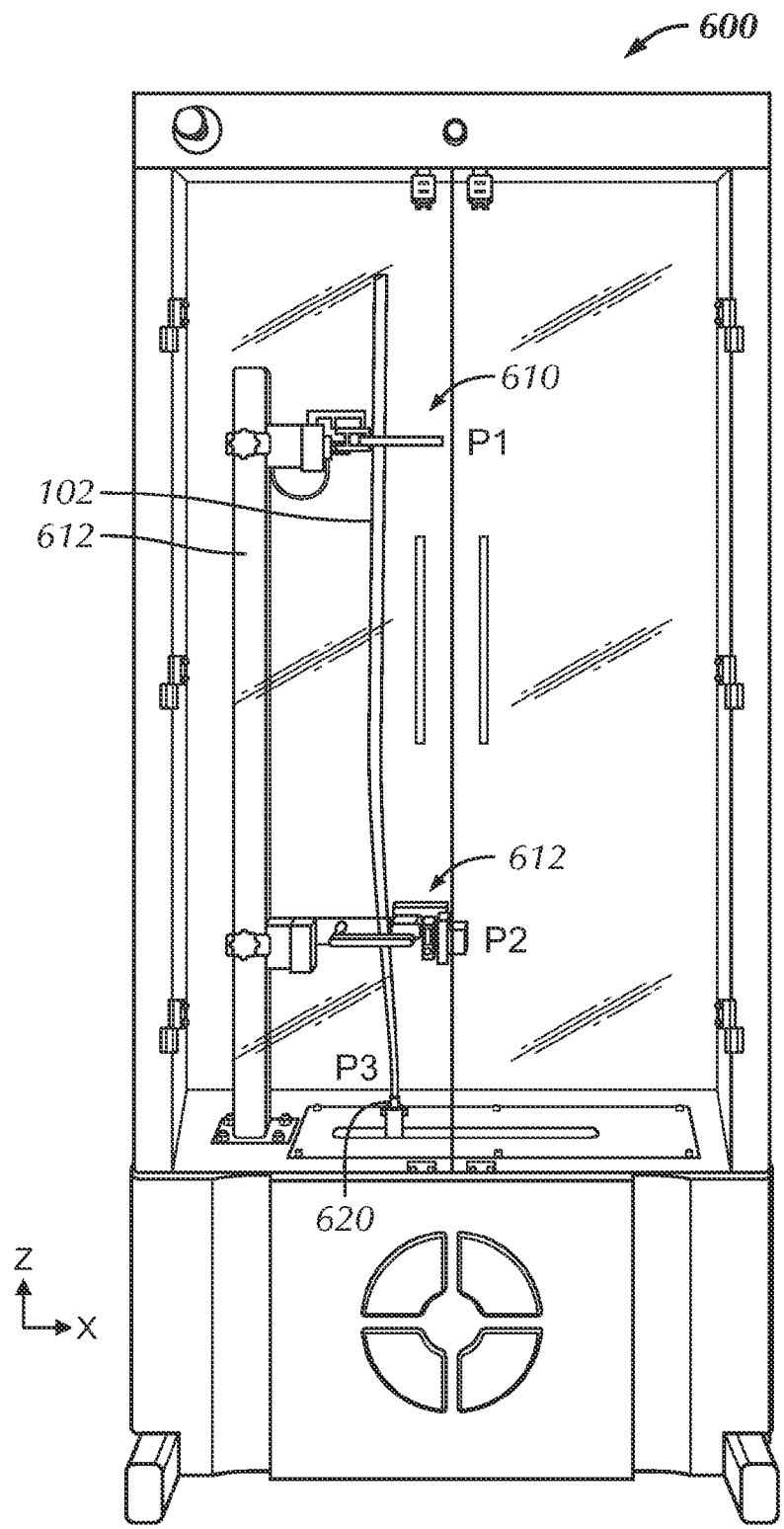
FIG. 7 is the shaft testing device of FIG. 6 in a loaded condition according to one embodiment.
Figure 8:
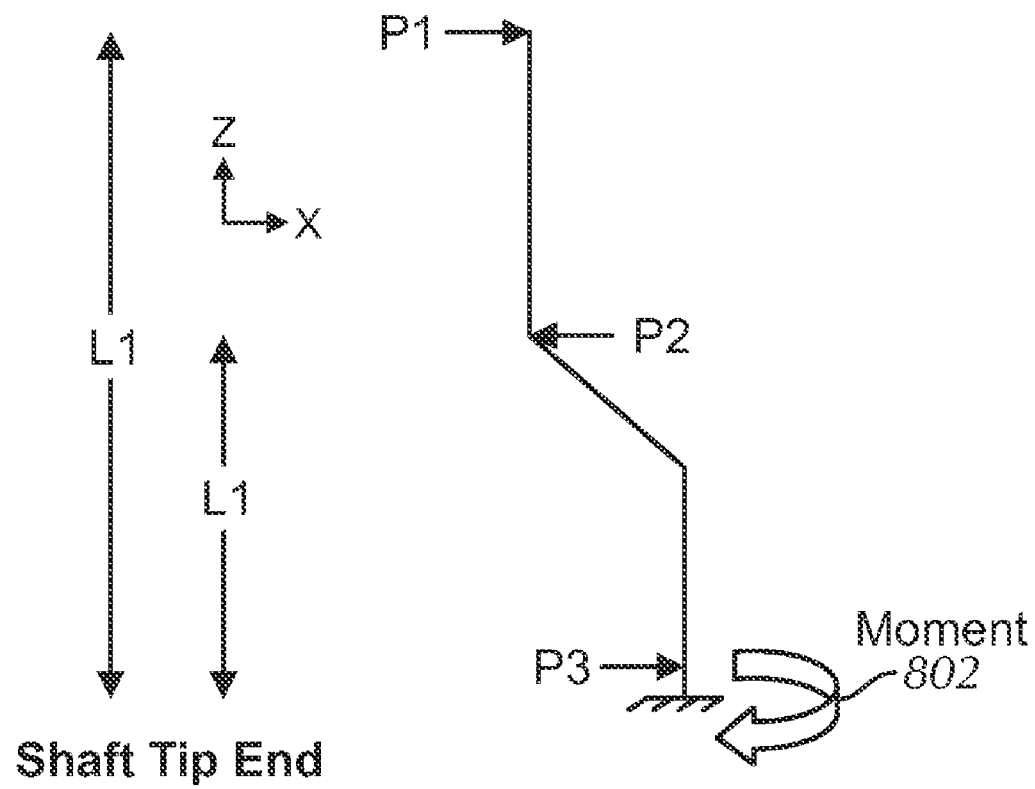
FIG. 8 is one embodiment of a free body diagram of the shaft testing device of FIGS. 6 and 7.
Figure 9:
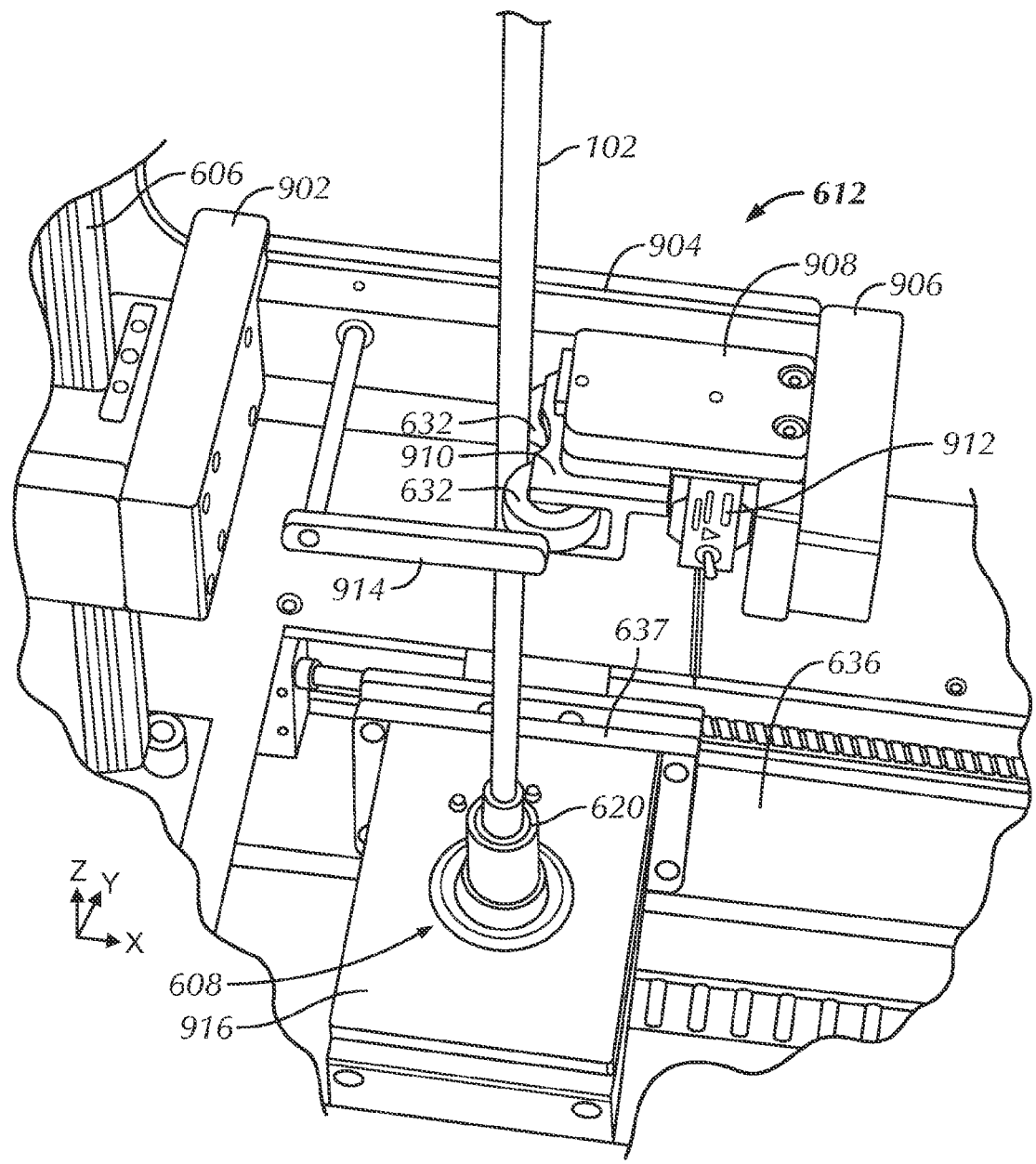
FIG. 9 is an enlarged view of a lower support assembly and a motor assembly and a linear assembly of the shaft testing device of FIG. 6 according to one embodiment.
Figure 10:
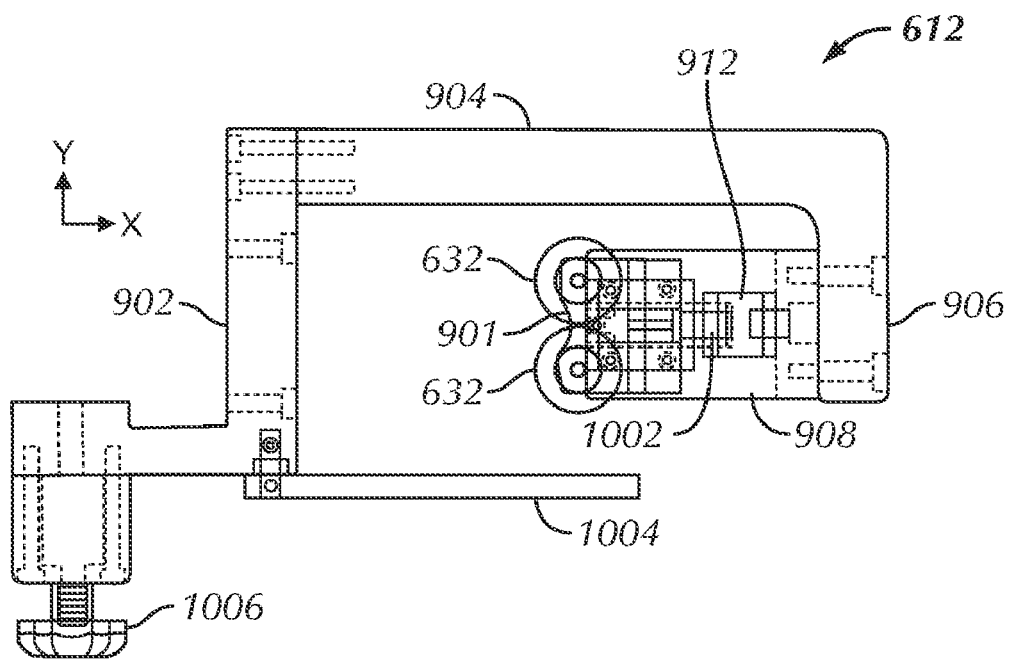
FIG. 10 is a top view looking at the x-y plane of a variation of the lower support assembly of FIG. 9.
Figure 11:
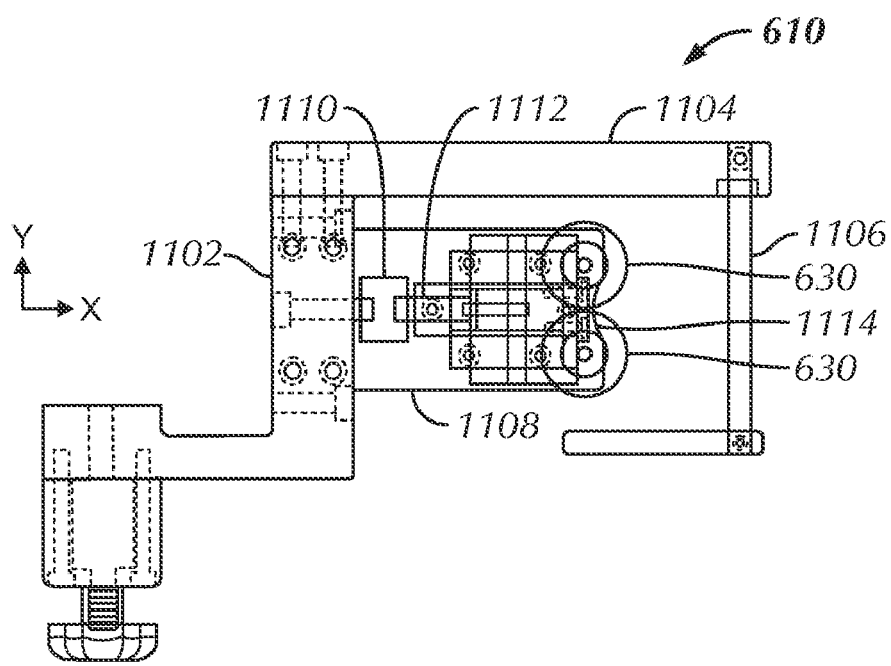
FIG. 11 is a top view looking at the x-y plane of the upper support assembly of the shaft testing device 600 of FIG. 6 according to one embodiment.

The shaft 102 is also supported in an upright position through contact with the upper support assembly 610 and the lower support assembly 612. In the illustrated embodiment, the upper support assembly 610 includes guide wheels 630 that engage one side (e.g., left side in the view of FIG. 6) of the shaft, while the lower support assembly 612 includes guide wheels 632 that engage an opposite side (e.g., right side in the view of FIG. 6) of the shaft. FIGS. 9-11 more clearly illustrate the upper support assembly 610 and the lower support assembly 612. The motor assembly 608 is mounted to a linear actuator assembly 634 including a linear motor 635 and a linear actuator 637 moveable about guide rails 636 such that motor assembly 608 including the shaft holder 620 moved to linearly moved along the x axis (see arrow 638) relative to the stationary upper and lower shaft supports 610, 612. The movement of the shaft holder 620 causes a deflection of the shaft between points 1, 2 and 3, labeled as P1, P2 and P3. The illustration of FIG. 7 shows the motor assembly in a loaded position causing the resulting deflection of the shaft 102. FIG. 8 illustrates a free body diagram of this deflection.

Similar to other embodiments described herein, the shaft is deflected in order to perform one or more tests on the shaft. In some embodiments, once deflected, the shaft is rotated, either partially or entirely and repetitively about the z axis (resulting in a moment 802 generated as illustrated in FIG. 8). The speed and direction of the rotation can be controlled by user defined parameters entered at the computer 628. It is noted that when the shaft is deflected, the shaft is securely held in position between the wheels 630 and 632 and the shaft holder 620 even though the wheels only engage one side of the shaft, respectively. The wheels maintain the portion of the shaft contacting the shaft support assembly in an x, y, z space, but allow for the shaft to rotate about the z axis. In one embodiment, the wheels 630, 632 are low frictions rotary devices that provide little resistance to rotation, but hold the shaft in location. The holder rigidly engages the tip end of the shaft in order to cause the shaft to rotate. It is noted that in one embodiment, the moment 802 is generated as Moment=(P2*L2)−(P1*L1), where P1 and P2 are the load cell values at locations P1 and P2, and L1 is the distance along the z axis from P3 to P1 and L2 is the distance along the z axis from P3 to P2.

According to several embodiments, the shaft testing device 600 includes an upper load cell 1110 and a lower load cell 912 (best seen in FIGS. 9-11). In this embodiment, a load cell is not used at the shaft holder 620 since the moment just above the shaft holder 620 can be calculated based on the load data at P1 and P2 given the known physical relationship and parameters. Each load cell measures the load as the shaft is rotated. The data output from the load cells is input to the computer 628 for processing and analysis.

Referring to FIG. 9, an enlarged view of the lower support assembly and the motor assembly and linear assembly of the shaft testing device 600 of FIG. 6 is illustrated. The lower support assembly includes brackets 902, 904, 906 and 908, wheel support 910, the load cell 912, and an arm 914. Bracket 902 couples to the linear guide rail 606. Brackets 902, 904 and 906 form a "C" about the shaft 102. Bracket 908 couples the wheel support 910 to the load cell 912. The wheel support 910 supports the wheels 632 and permits free rotation. The arm 914 serves as a guide and safety measure if the shaft fails under load. Also clearly seen in FIG. 9 is the shaft holder 620 of the base support 604. The shaft holder 620 coupled to the motor shaft through a hole on in plate 916 such that the shaft holder 620 rotates relative to the stationary plate 916. The plate 916 rigidly couples to the linear actuator 637, which moves linearly about the linear guide rails 636. As the linear actuator 637, plate 916 and the shaft holder 620 move in the x direction (e.g., to the right in FIG. 9), the shaft is deflected or loaded about the lower support assembly 612 and the shaft holder 620. Load measurements are taken by the load cell 912. A top view in the x-y plane is shown of a variation of the lower support assembly in FIG. 10 and illustrating a load cell coupling 1002 and variation of the arm 1004. The lower support assembly of FIG. 10 includes a knob that can be tightened to secure the lower support assembly to the guide rail 606.

Referring to FIG. 11, a top view is shown of the upper support assembly 610 of the shaft testing device 600 of FIG. 6. The upper support assembly 610 includes brackets 1102, 1104, 1108, wheel support 1114, the load cell 1110, load cell coupling 1112 and an arm 1106. Bracket 1102 couples to the linear guide rail 606. Brackets 1102 and 1104 provide the main support from the assembly 610. Bracket 1108 couples the wheel support 1114 to the load cell 1110 via the load cell coupling 1112. The wheel support 1114 supports the wheels 630 and permits free rotation. The arm 1106 serves as a guide and safety measure if the shaft fails under load. Load measurements are taken by the load cell 1110 and output to the computer 628 for processing.

It is noted that in some embodiments, the shaft testing device only includes one support assembly, instead of both an upper and lower support assembly 610, 612. In this case, the shaft holder 620 displaces one portion of the shaft (e.g., the tip portion) relative to the other portion of the shaft held by the other shaft support assembly. Once displaced, the shaft may be rotated while taking load measurements.

In accordance with one or more embodiments, the shaft testing devices described herein may be operated in one or more modes. For example, the shaft testing device may operate in a 'static bend mode' in which a portion of the shaft is deflected until the shaft breaks or fails. For example, referring to the embodiments of FIGS. 6-11, the motor assembly 608 is laterally moved along the x axis in defined increments causing a deflection of the shaft about P1, P2 and P3 until the shaft fails. From this test, it can be determined at what load and displacement the shaft will fail. In this embodiment, the shaft is not rotated. In a 'static bend with rotation mode', one portion of the shaft is incrementally deflected relative to another portion of the shaft. At each increment amount of deflection, the shaft is completely rotated at a slow speed to see if the shaft will fail. If the shaft does not fail, the portion of the shaft is further deflected in the next incremental amount and rotated again. The process is repeated until the shaft fails. For this test, angular orientation of failure is determined. In a 'fatigue test mode', one portion (e.g., the tip end) of the shaft is deflected (e.g., laterally along the x axis) relative to another portion of the shaft (e.g., the butt end of an intermediate portion). Once deflected to a desired load, the shaft is continuously and repetitively rotated at a defined number or revolutions per second for a desired number of cycles or until the shaft fails. In this manner, a user can determine how many cycles before the shaft fails under different load conditions.

During one or more of the test modes, load cell data, and linear and rotary encoder measurements are output to the controller 216 or computer 628 for processing. Load cell data may be taken at or adjacent one or more locations of the shaft supported by a shaft support or shaft holder, such as those described herein. In preferred form, load cell data is collected at the portion of the shaft at or near the tip end, which in use is the area of the shaft that experiences the most loading forces. Additional load cell data may be obtained from other portions of the shat, such as the upper and lower support assemblies 610 and 612 or the chuck 204 and intermediate support 104. Other data output to the computer may include rotation speed, the number of revolutions or cycles, a moment calculated at a given load location, etc.

Figure 12:
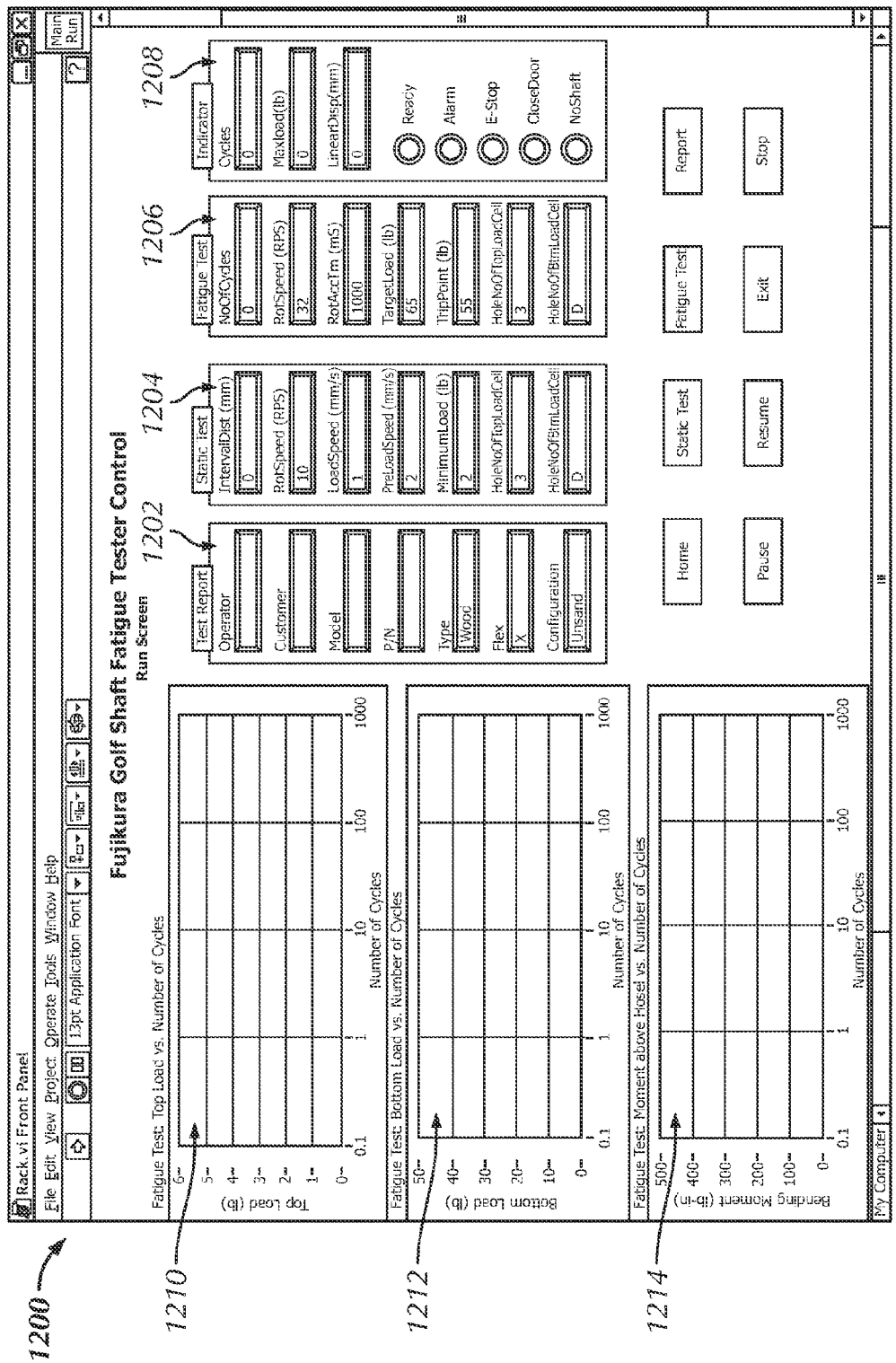
FIG. 12 is a user interface for an application controlling a controller of the shaft testing device of FIGS. 6-11 in accordance with one embodiment.

Referring next to FIG. 12, a user interface is shown for an application running on the computer 628 and controlling a controller of the shaft testing device of FIGS. 6-11 in accordance with one embodiment. It is understood that the user interface is generated and caused to be displayed by a software application stored on the computer or remotely stored but executed at least in part on the computer. In one embodiment, the application was developed using by LabView, a well known commercially available software development tool. The user interface 1200 includes parameters that may be entered by an operator, e.g., within fillable fields. Data under the test report region 1202 includes basic information entered by the use including operator, customer, model, part number, type of shaft, flex (e.g., level of shaft stiffness), and configuration.

The static test region 1204 includes parameters when performing the static bend mode and the static bend with rotation mode. The IntervalDist (mm) field allows the user to define the spacing between lateral displacements of one portion of the shaft relative to another portion in millimeters. In other words, it defines the distance between displacement steps. The RotSpeed (RPS, revolutions per second) defines the rotational speed. This value will be set to '0' in the event a 'static bend mode' test is performed, but will be set to a value when performing a 'static bend with rotation mode' test, which is preferably a value less than 1.0 to slowly rotate the shaft. The LoadSpeed (mm/s) field defines the velocity of the loading or deflection. The PreLoadSpeed (mm/s) field defines the speed of linear actuator movement when moving to initially engage the shaft prior to causing a deflection. The MinimumLoad (lb) field defines the minimum load or preload that is applied prior to deflection. The HoleNoofTopLoadcell field defines the vertical height of the upper support assembly 610 and in particular, the load cell 1110. In particular, it indicates which hole 614 the upper support assembly engages. Similarly, the HoleNoofBtmLoadcell field defines the vertical height of the lower support assembly 612 and in particular, the load cell 912. In particular, it indicates which hole 614 the lower support assembly engages. The upper holes are labeled by number and the lower holes are labeled by letter to avoid confusion.

The fatigue test region 1206 includes parameters when performing the fatigue test mode. The NoOfCycles field defines how many complete revolutions the shaft will rotate under load, typically, this number will be several thousand cycles. If the number is '0', the shaft will rotate indefinitely until failure or until the user terminates the test. The RotSpeed (RPS, revolutions per second) defines the rotational speed. This value will preferably be a value greater than 1.0 to quickly rotate the shaft. The RotAccTm (ms) field defines the time for the motor 624 to reach the user defined rotation speed, i.e., it defines the acceleration of the rotation. The TargetLoad (lb) field defines the load cell value that should be reached by the deflection of the shaft. For example, the tip end of the shaft will be deflected until the load cell at the shaft holder 620 reaches the target load, e.g., 20 pounds, The TripPoint (lb) field defines the load measurement in order for the system to declare a failure. For example, in operation, the shaft will be deflected to a load of 20 pounds and rotated. After many thousands of rotations, the shaft will fail, which will be indicated by a reduction in the load cell measurement after the point of failure. In this example, the default trip point is set at 0.5; however, in most cases, the trip point should be set to about 10 lbs less than the target load. Thus, in one example of FIG. 12, the trip point would be set to 10 lbs so that when the measured load drops to 10 or fewer lbs, the system declares a failure. Like the static test field 1204, the HoleNoofTopLoadcell field and the HoleNoofBtmLoadcell field define the vertical height of the load cells of the upper and lower support assemblies 610 and 612.

The indicator region 1208 provides the status of the operation of the system, such as indicating the number or rotations thus far, the max load, the linear or lateral displacement or deflection. This region 1208 also includes lights to indicate if the shaft testing device is ready, an alarm condition exists, an electronic stop occurred, that a door closing off the frame is closed and when there is no shaft present.

In some embodiments, the user interface 1200 includes real time plots of the data collected during a given test. Region 1210 provides the load cell measurements from the load cell 1110 of the upper support assembly 610 as load values vs. number of cycles. Region 1212 provides the load cell measurements from the load cell 912 of the lower support assembly 612 as load values vs. number of cycles. Region 1214 provides a calculated moment at a portion of the shaft proximate the point of entry of the shaft into the shaft holder 620, e.g., just above the shaft holder 620 vs. the number of cycles. This value is calculated based on the measured load cell values and defined relationship between the various components. It is well within the ability of one of ordinary skill in the art to calculate such a moment. For example, in one embodiment, referring to the free body diagram of FIG. 8, the moment 802 is calculated as $(P2*L2)-(P1*L1)$.

Figure 13:
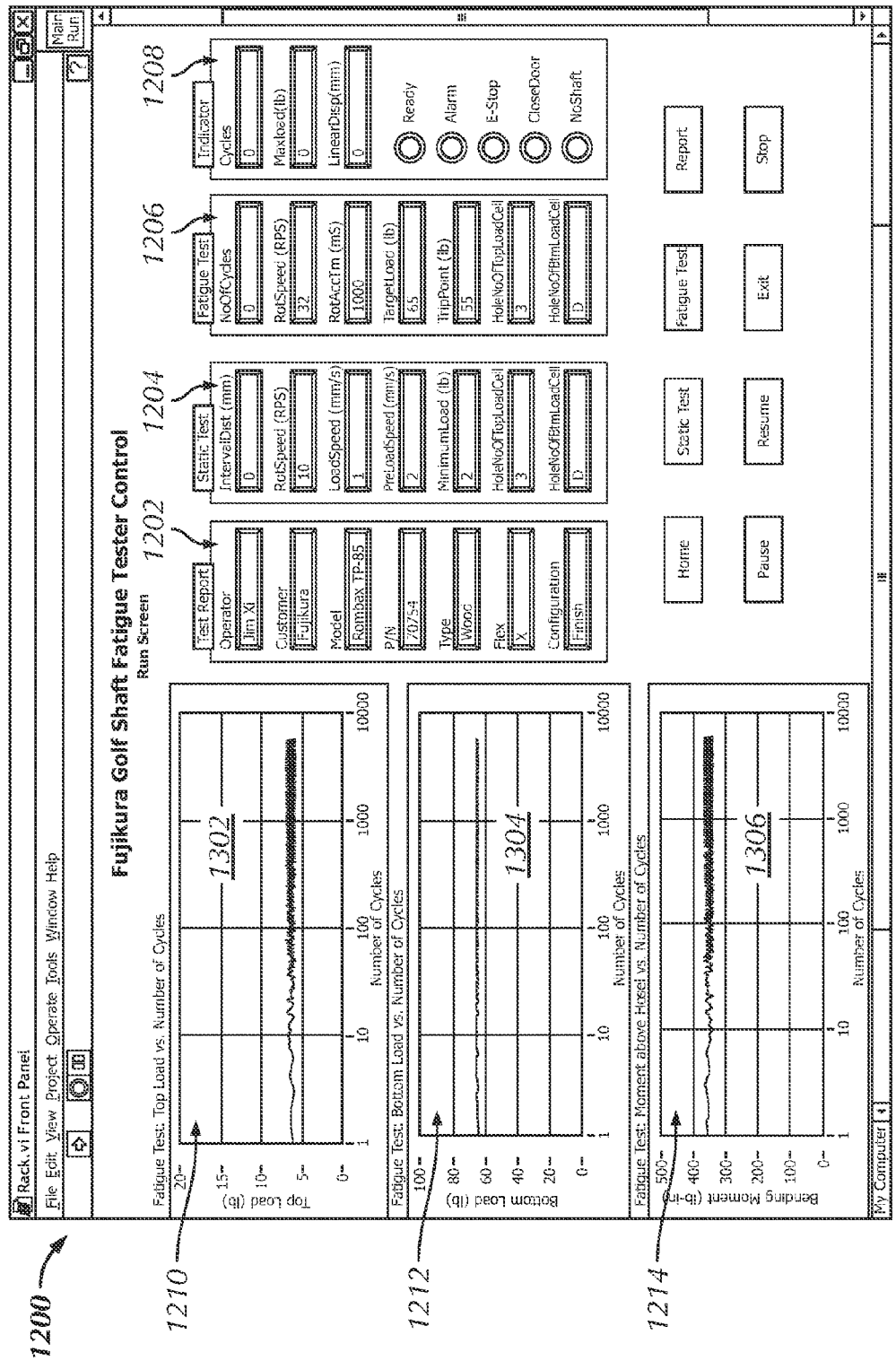
FIG. 13 is a variation of the user interface of FIG. 12, and including plots for the data collected and calculated according to one embodiment.

FIG. 13 illustrates one sample fatigue test mode including plots for the data collected and calculated. In this test, the shaft is laterally deflected to a load of 65 lbs and rotated at 32 revolutions per second. The resulting data is plotted as lines 1302, 1304 and 1306, respectively. So far in the test, no failure has occurred. A failure would be declared by the system in the event the load measurements at the shaft holder 620 drop to 55 lbs. This level will not result in the shaft breaking, but results in a breakdown in the rigidity of the shaft to the point that the shaft will not perform as expected.

According to several embodiments, load cell measurements and/or rotational (and/or angular) position measurements are output to the controller and/or computer for display, storage and/or processing. In some embodiments, the load of a shaft is measured and plotted over time (in terms of revolutions at a certain rotation frequency). For example, TABLE 1 below shows the first ten entries of data collected by one embodiment of a tester (such as illustrated in FIGS. 1-5) testing a golf shaft being rotated at 15 revolutions per second (15 rps) with an initial lateral deflection of the tip end relative to the butt end producing a load of approximately 27 lbs. Generally, load measurements are recorded approximately every 300 cycles (revolutions). In this example, the measurements are not taken at exactly the same circumferential location; however, in other examples measurements may be taken at the same circumferential location or locations about the shaft.

TABLE 1

| Load (units) | Load (lbs) | Cycles |
| --- | --- | --- |
| 570 | 27.832 | 0.038 |
| 544 | 26.807 | 299.922 |
| 565 | 26.172 | 600.572 |
| 565 | 26.514 | 901.215 |
| 539 | 26.709 | 1201.858 |
| 545 | 26.611 | 1502.507 |
| 561 | 27.49 | 1803.162 |
| 538 | 27.002 | 2103.802 |
| 541 | 26.807 | 2404.452 |
| 563 | 26.758 | 2705.1 |
| ... | ... | ... |

Figure 14:
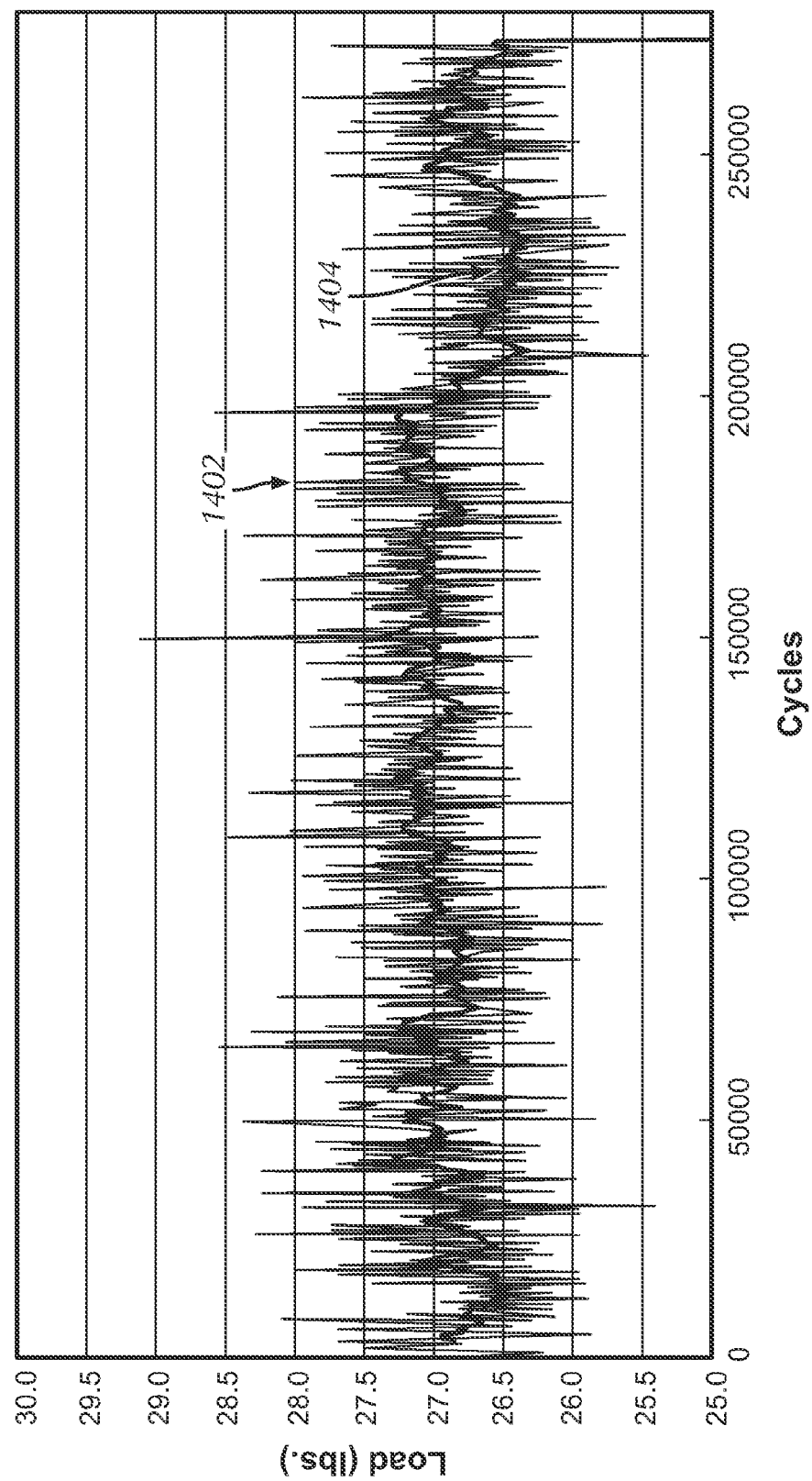
FIG. 14 is a graphical plot of load in lbs. vs. cycles of the data collected until the shaft fails in accordance with one embodiment of the invention.

FIG. 14 illustrates a graphical plot of load in lbs. vs cycles (number of revolutions) of the data collected until the shaft fails (i.e., breaks, the load drops to zero). For example, the plot of FIG. 14 is a finer resolution example of the plots of regions 1210 and 1212 of FIGS. 12 and 13. It is noted that to generate the data for FIG. 14, TABLE 1 continues for thousands of cycles (only the first tens entries being illustrated).

As can been seen, line 1402 represents the actual data collected and in this case, this data varies within 2 lbs until the shaft fails at just under 300,000 revolutions. Line 1404 is a moving average line reflecting the average of 10 measurements. It is apparent that differently designed shafts (different materials, stiffness, etc.) will have a different load profile, while in some embodiments, it is desired that different shafts of the same design will have the same profile. In some embodiments including one or more of the embodiments described throughout this specification, the data is processed, saved and output for display for a user, for example, using a computer having a processor, memory and software, firmware, or other machine readable instructions to process and display the data. In some embodiments, the information represented in TABLE 1 and FIG. 14 is used for a variety of purposes. For example, it is possible to test a shaft and determine its fatigue life, and additionally compare it relative to other shafts. It may also be possible to analyze the data to determine points in time that indicate the approaching failure of a shaft (perhaps a sudden change in load prior to failure). Similar to the plot of region 1214, the plot could alternatively be a calculated moment vs. number of revolutions.

Figure 15:
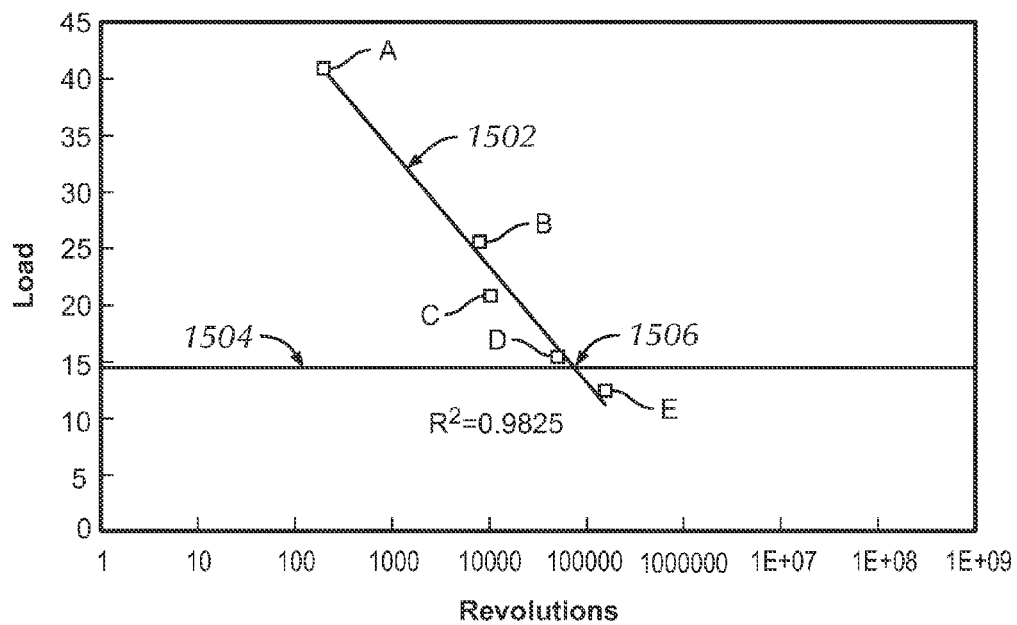
FIG. 15 is a semi-log plot of load in lbs vs. revolutions at which the shaft failed at that load using a tester such as shown in FIGS. 1-5 or FIGS. 6-11 according to one embodiment.

In some embodiments, a shaft is tested under different loads. Referring next to FIG. 15, a semi-log plot is shown of load in lbs vs revolutions (in this case, at 15 rps) at which the shaft failed (broke) at that load using a tester such as shown in FIGS. 1-5 or FIGS. 6-11. For example, a first shaft is deflected or bent to a load of approximately 42 lbs and then rotated until the shaft fails. In this case, the shaft failed at point A at about 200 revolutions (the x axis is in log scale). Then second shaft (which should be identical to the first shaft) is loaded to about 25 lbs (i.e., deflected less than the first shaft) and rotated until it failed at point B at about 10,000 revolutions. A third shaft loaded to about 21 lbs failed at point C also at about 10,000 revolutions. A fourth shaft loaded to about 15 lbs failed at point D at about 50,000 revolutions. And a fifth shaft loaded to about 13 lbs failed at point E at about 100,000 revolutions. Based on this information, a straight line 1502 is drawn based on points A-E which closely approximates the fatigue life of that particular shaft at any load. Statistically, the $R^2$ value approximates how closely line 1502 matches the measured data, and in this case, $R^2$=0.9825, where 1.0 is ideal. Using this information, one can estimate what the expected fatigue life of a shaft will be under certain loads. This information can be helpful in determining if a particular shaft is well suited for an intended application (intended deflection or load) and intended lifetime of the shaft in use. While FIG. 15 illustrates only 5 test points, it is possible to generate such a line (e.g., load vs fatigue profile) from fewer or more than the 5 points. For example, using a plurality of identical or substantially identical shafts and a tester machine such as disclosed herein, it can be determined at what load the shaft will statically fail (no revolutions), and then begin testing for fatigue at certain percentages of that static failure load. For example, if it is determined that a given shaft statically fails with a 50 lb deflection load (i.e., the shaft is deflected without rotation until it fails), then the first shaft is tested under load and rotation at 90% of that load, the second shaft at 80% of that load, the third shaft at 70% of that load, and so on. It is noted that these percentages are by way of example, and other percentages and techniques may be used to determine what load test points would be used in generating a profile (e.g., line 1502).

Furthermore, in cases where the $R^2$ value indicates a good fit (such as where $R^2$=0.9825 in FIG. 15), in some embodiments, the resulting line is used to extrapolate failure points at numbers of revolutions not actually tested. For example, in some embodiments, a number of test points may be determined, each having a low number of revolutions/cycles (e.g., 100-1000 revolutions), to generate the profile (line 1502) and then extrapolate what the load failure will be at larger numbers of revolutions (e.g., at 10,000-100,000 revolutions) without actually having to determine these test points, saving time in generating the load vs. fatigue profile.

Additionally, still referring to FIG. 15, knowing the load vs. fatigue profile of the shaft, a threshold may be defined in terms of the load that is sufficient to cause the shaft to fail during normal intended use of the shaft. By knowing where this load threshold crosses the load vs. fatigue profile (line 1502), it can be estimated the life of the shaft in its intended use. For example, in one embodiment of a shaft used in a golf club, it is assumed (for sake of example) that the load threshold is 15 lbs. A horizontal threshold line 1504 then exists on the graph of FIG. 15 at 15 lbs. This is the example load that would normally cause the shaft to fail with the use of the shaft within a golf club striking a golf ball. Once the profile (line 1502) is determined or estimated, the point 1506 at which the load threshold 1504 crosses line 1502 determines the life of the shaft. According to the graph of FIG. 15, this would occur at about 50,000-70,000 cycles (revolutions). That is, at below the number of cycles or revolutions of point 1506, the shaft would not fail, but at or above the number of cycles or revolutions of point 1506, the shaft will fail.

Figure 16:
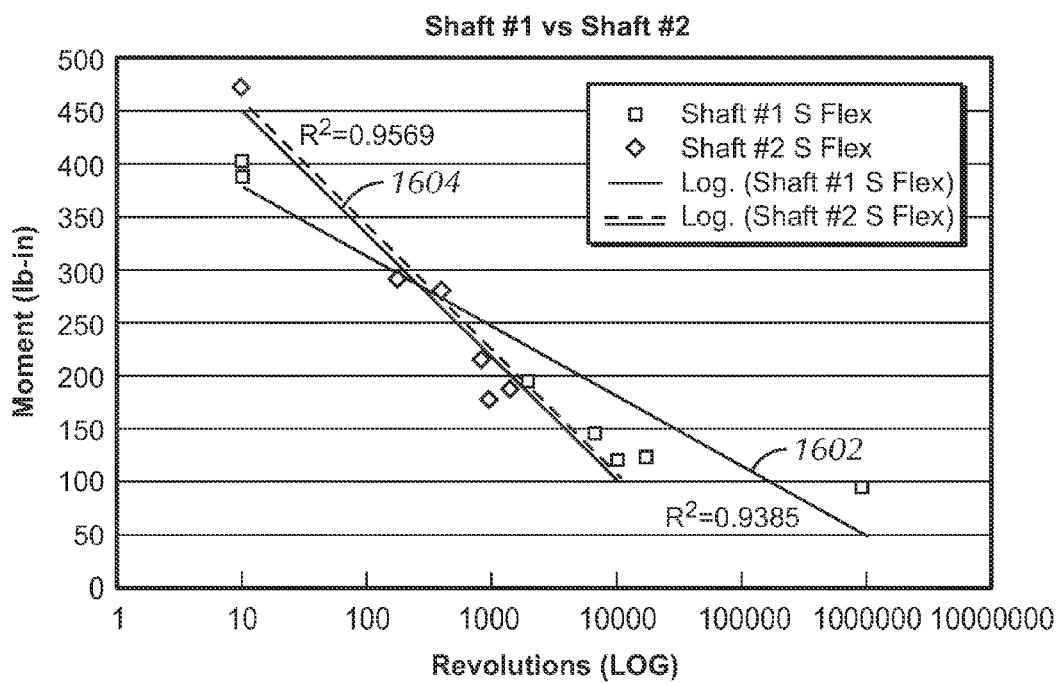
FIG. 16 is a variation of the plot of FIG. 15 providing a semi-log plot of moment in lbs-in vs. revolutions according to one embodiment.

Referring next to FIG. 16, a variation of the plot of FIG. 15 is shown as a semi-log plot of moment in lbs-in vs. revolutions. Instead of plotting load, a moment is calculated, such as at point P3 and plotted. This plot may be used for similar purposes as the plot of FIG. 15. It is noted that the plot of FIG. 16 includes the plots of two different model shafts (shaft #1 and #2) designed to have different flex characteristics. As can be seen, lines 1602 and 1604 illustrate the moment vs. fatigue profile for the two shafts, each having a different $R^2$ value. In other embodiments, multiple different shafts of the same model may be tested to generate statistically more accurate profiles, for example, by averaging the failure points and moments for each shaft. For example, this would yield an average number of revolutions for failure at a given test moment. These average values should provide statistically more accurate profiles.

The following description provides one specific example of the operation of an embodiment of a shaft testing device. It is understand that this is provided for example, only and that other embodiments may operate differently. This example refers to the embodiment described in FIGS. 6-11. In this example, the shaft testing device supports the following modes: power on; standby to save power, resume, pause/interruption; emergency stop; cancel, and power off. The shaft testing device of this example provides the following modes: (I) static bend mode; (II) fatigue test mode; and (III) fatigue life mode which predicted life of shaft before failure.

In the static bend mode (mode I), the user inputs include: part description; shaft number; part type (Driver, Fairway, Hybrid, or Iron); operator name; date (mm/dd/yy); rotation speed (rpm) (zero if not rotating); interval displacement or load between rotation; load to reach before rotations at intervals will occur (kg or N); displacement Speed (mm/min); and failure definition (% of load drop). The sensor inputs include: doors open or closed (two doors); home and maximum displacement positions; locations of upper and lower wheel supports; load cell readings at the upper and lower wheel supports; and Emergency Stop condition. The outputs include: shaft tip position from home (mm); load from load cells (kg or N); calculated moment at shaft tip (kg*m or N*m); effective tip stiffness: slope of calculated load at tip divided by displacement (kg/m or N/m); max load (kg or N); max displacement (mm); max moment (kg*m or N*m); shaft radial orientation at failure (Deg); chart of applied calculated moment vs. displacement or applied load at tip vs. displacement. The general sequence of events in this embodiment is as follows. First, the Static Bend Test is selected from the user interface. The interface prompts the user to adjust the support wheels to their proper location, load a shaft into the machine, and shut the doors. Then, the user interface prompts for user inputs. If rotation speed is nonzero, user must specify: rotation interval; and load or displacement to reach before rotations will occur. The user inputs loaded. The electrical components are powered on, light mode is set to bright and door sensors are checked. If any door is open: the interface prompts user to shut the doors; all machine movement is restricted until the door is closed.

When the doors are shut, the interface prompts the user if they'd like to Resume or Cancel the test. Next tare (zero out) the load cells. The linear actuator then displaces the shaft. Establish the '0' location (separate from Home position) when the Load cells see the first load. If no loading is seen while part is moving, stop after X movement and prompt user that no part is in fixture or there is an error. If rotation speed is zero, continue displacement until failure criteria is met. If at any time the displacement stays in one location for Y time then initiate the stop sequence and warn the user that the strength of the shaft exceeds the machine's capability. Nest, stop and maintain displacement at failure. Output data is required. If rotation speed is nonzero and the load is reached to begin rotations, rotate the part 360°. When the rotation is complete, displace the part to the next interval displacement or load, stop, and rotate again. Repeat until failure criteria is met. Stop and maintain displacement at failure. Output required data. If the max displacement sensor is triggered before the failure criteria is met: Stop the displacement at the max displacement location; User interface alerts user that max displacement has been reached; and Output load at maximum displacement. The user interface communicates test is complete and prompts user to save data. The user interface prompts user to bring the linear actuator back to the Home position (allows the user to investigate the break under loading, if desired). If Yes to above, linear actuator returns home (2 unique speeds to return home).

Regarding the fatigue test program mode (mode II), the user inputs are as follows: Part description; Shaft number; Part Type (Driver, Fairway, Hybrid, or Iron); Operator name; Date (mm/dd/yy); Rotation speed (rpm); Acceleration of rotation; Test load/moment; Test to failure including defining failure criteria; Test to cycle count including inputting max cycles to test to; Displacement Speed High (mm/min); and Displacement Speed Low (mm/min). The sensor inputs are as follows: Doors open or closed (two doors); Home and maximum displacement positions; Locations of upper and lower wheel supports; Load cell readings at the upper and lower wheel supports; and Emergency Stop condition. The outputs are as follows: Shaft tip position from home (mm); Measured Loads from load cells (kg or N); Calculated moment at shaft tip (kg*m or N*m); Effective tip stiffness: Slope of calculated load at tip divided by displacement (kg/m or N/m); Shaft Displacement (mm); Shaft radial orientation at failure (Deg); Cycles; Test time (hours:min); Chart of applied calculated moment vs. displacement or applied load at tip vs. cycles. The general sequence of events in this embodiment is as follows.

First, the fatigue test mode is selected from the user interface. The user interface then prompts the user to adjust the support wheels to their proper location, load a shaft into the machine, and shut the doors. The user interface then prompts for user inputs. If "test to failure' is chosen, the user must specify Failure criteria. If the "test to cycle" is chosen, the user must specify: Max cycles for test. Next, user inputs are loaded and all electrical components are powered on. The light mode is set to Bright. Next, door sensors check status of doors. If any door is open: the interface prompts user to shut the doors; and all machine movement is restricted until the door is closed. When the doors are shut, the interface prompts the user if they'd like to Resume or Cancel the test. Next, Tare the load cells. Next, the linear actuator displaces shaft at high speed until Y load is reached (for speed efficiency). After Y load is reached, the linear actuator displaces the shaft at low speed (for loading accuracy). If no loading is seen while part is moving, stop after X movement and prompt user that no part is in fixture or there is an error. If at any point the either of the Load Cell loads reaches 80% of capacity (in this case 80 lbs), stop the sequence and warn the user. When the user input target is reached, the main motor spins the shaft one revolution slowly, taking load measurements at all circumferential positions (all 360°). The PLC determines which angular position associates with the max load and establishes that point as the 0° location. The main motor then spins the shaft to the 0° location (this position directly facing the load cell). Next, accelerate the shaft to user input RPM requirement. If the maximum travel sensor is activated, stop displacement and the user interface alerts user maximum travel has been reached and test load must be lowered or test can be performed at the max travel. Next output rates are defined. If the failure criteria or cycle count is reached, stop rotations. The user interface communicates the test is complete and prompts user to save data. The user interface then prompts user to bring the linear actuator back to the Home position (allows the user to investigate the break under loading, if desired). If Yes, then the linear actuator returns home (2 unique speeds to return home).

The fatigue life test program mode (mode III) is an automated procedure that guides the user through Mode I and Mode II to create a semi-log fatigue life chart. Referring to the flow chart 1700 of FIG. 17, Mode I will run in a loop until the operator chooses to exit the loop. For example, the user will load a part (shaft) for testing according to mode I (Step 1702), run mode I (Step 1704) and decide whether to repeat the test (Step 1706). Mode II will run at specifically calculated loading conditions, $L_Y$, where Y is the number of loading conditions and ranges from 3 to 10 (with 4 as a default value). When one loading condition test is completed (i.e., the answer to decision Step 1708 is no, the system will move to the next loading condition (Step 1710) and so forth until all loading conditions are completed (this is called the $L_Y$ Loop). Within each loading condition test (i.e., within each value of Y) is a loop that repeats Mode II for the same loading condition (this is called the Mode II Loop). For example, the user will load a part (shaft) for testing according to mode II (Step 1712), run mode II (Step 1714) and decide whether to repeat the test (Step 1716) while maintaining the same loading condition (Step 1718). Therefore, each loading condition tested contains one or more tests at that specific loading condition.

For mode III, all inputs and outputs are the same as described in Modes I and II. However, since Mode III is a combination of both Modes I and II, the user will need to enter all required inputs for both Modes I and II prior to initiating the test. As Mode III runs through its program sequence, inputs provided prior to initiating the test are not required to be re-entered. Again, the flowchart of FIG. 17 provides a general flow of Mode III.

A more specific sequence for the Mode I loop of the flowchart of FIG. 17 according to one embodiment is as follows. (a) The user interface requests required inputs for both Mode I and Mode II operations. Then, (b) the user interface communicates to the user that a Static Break Test will initiate and prompts the user to load the shaft into the shaft testing device. (c) Mode I will execute as described above. (d) After the mode I test is complete, the user interface: displays the test results; asks if the user accepts the results or would like to delete the test; and prompts the user if they'd like to run another test to obtain averages and statistical values. If the user chooses to accept the single test data and move on, exit the Mode I loop and go to the Mode II loop. If the user chooses to repeat another test, repeat (b) through (c) above. (e) Whenever more than one test is complete, the user interface: Displays the test history within the Mode I loop; Displays the test results from the latest test; Displays the statistical information from the total number of tests; Asks if the user accepts the results or would like to delete any of the tests; and Prompts the user if they'd like to run another test to obtain better averages and statistical values. If the user chooses to accept the statistical data and move on, exit the Mode I loop and go to the Mode II loop. If the user chooses to repeat another test, repeat (b), (c), and (e) above.

A more specific sequence for the Mode II loop of the flowchart of FIG. 17 according to one embodiment is as follows. (a) Mode II uses the Static Break data to automatically set up the Mode II tests at different loading conditions. (b) The user interface allows the user to choose how many different loading conditions, Y, they want to run (between 3 and 10, default value at 4). (c) The user interface communicates to the user that a Fatigue Test will initiate at load $L_y$ and prompts the user to load the shaft into the shaft testing device. (d) Mode II will execute as described in the Mode II section. (e) After the test is complete, the user interface: Displays the test results; Asks if the user accepts the results or would like to delete the test; and Prompts the user if they'd like to run another test to obtain averages and statistical values. If the user chooses to accept the single test data and move on, exit Mode II and go to the $L_y$ Loop. If the user chooses to repeat another test, repeat (c) (d) above at the same loading condition, $L_Y$ (Mode II Loop). (f) Whenever more than one test is complete, the user interface: Displays the test history within the Mode II loop; Displays the test results from the latest test; Displays the statistical information from the total number of tests in the $L_Y$ loop; Asks if the user accepts the results or would like to delete any of the tests; and Prompts the user if they'd like to run another test to obtain better averages and statistical values. If the user chooses to accept the single test data and move on, exit Mode II and go to the $L_y$ Loop. If the user chooses to repeat another test, repeat (c) (d) above at the same loading condition, $L_Y$ (Mode II Loop).

Figure 17:
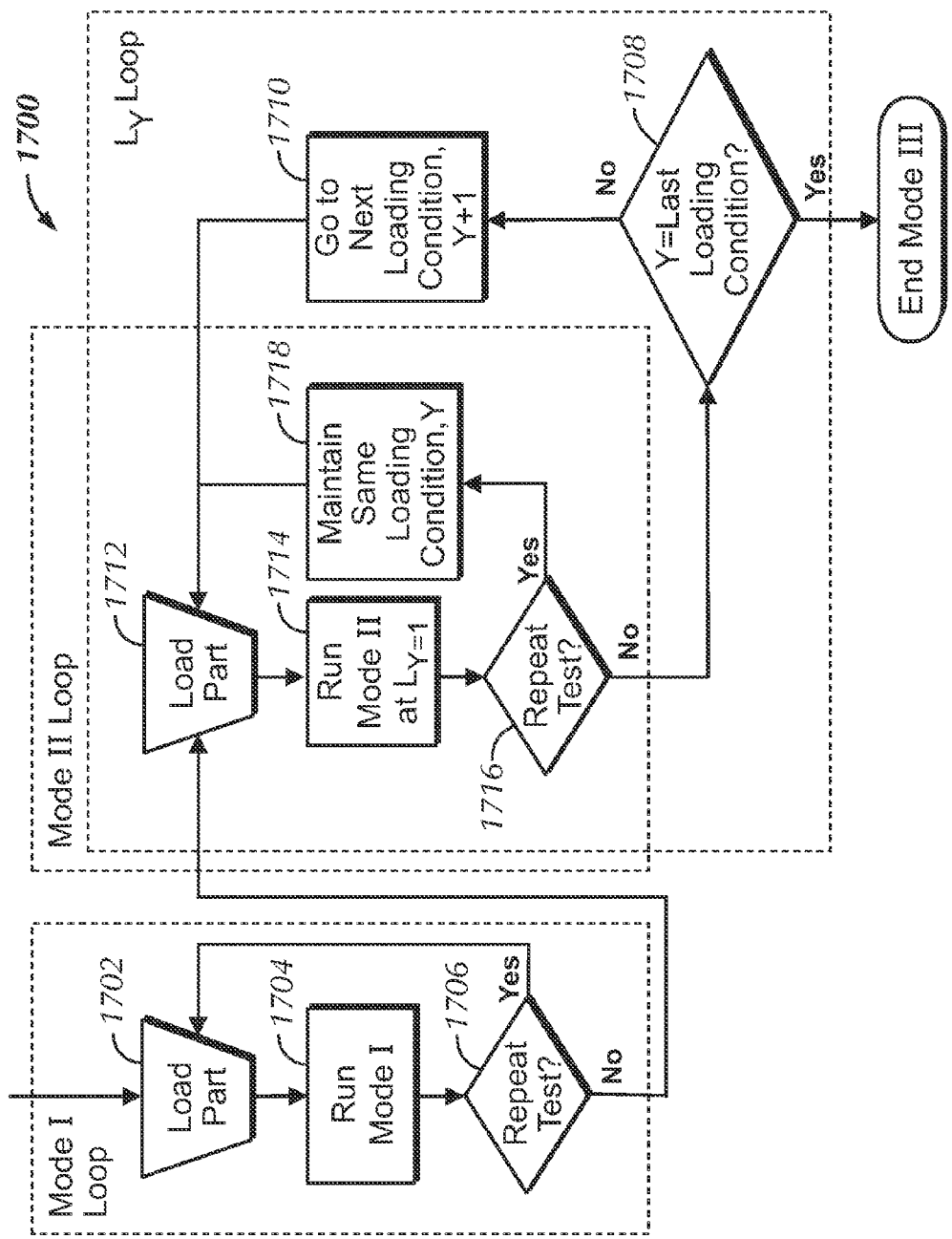
FIG. 17 is a flow chart of the steps performed in the operation of a shaft testing device in accordance with an embodiment of the invention.

The $L_y$ Loop of FIG. 17 repeats the same functions as the Mode II loop but increments the different loading conditions, Y, until the last Y is completed. Data from the Static Break Test and Fatigue Life Tests are charted in a semi-log plot continuously as the data is gathered for immediate, real-time review by the operator. The chart should serve as a guide to the operator whether to repeat, delete, or accept tests.

Turning now to several additional embodiments, shaft testing devices are provided that test for torsional fatigue of the shaft. One factor in the overall strength of a shaft is its torsional fatigue strength. Torsional fatigue strength of a shaft is relevant in the golf industry because a golf shaft, when in use, has a torque repeatedly applied to it. Thus, for this and other reasons, there is a need to be able to simply and accurately determine the torsional fatigue strength of a shaft.

In some embodiments, a device for evaluating the torsional fatigue of a shaft is provided comprising a frame; a first holder coupled to the frame, the first holder adapted to hold a first portion of a shaft; a second holder coupled to the frame, the second holder adapted to hold a second portion of the shaft; and wherein the second holder is adapted to introduce an angular displacement of the second portion of the shaft relative to the first portion of the shaft.

Some embodiments provide a method for testing torsional fatigue of a shaft comprising holding a first portion of a shaft; holding a second portion of the shaft; and angularly displacing the second portion of the shaft relative to the first portion.

In some embodiments, a torsional testing machine and related methods are provided to test the strength of a shaft under the strain of bidirectional oscillating angular displacement, similar to the force on a golf shaft when in use. Angular displacement refers to an amount of rotation of an object about an axis and may also be referred to as rotational displacement. In some embodiments, at least two portions (e.g., two ends) of the shaft are held while one portion is angularly displaced relative to the other portion in order to determine a torsional breaking point of the shaft. In some embodiments, a first portion and a second portion of the shaft are held while an angular displacement is applied to the second portion in order to generate a profile of the torsional fatigue life of the shaft. Generally, in some embodiments, when testing the torsional fatigue life of a shaft, at least two portions (e.g., ends) of the shaft are maintained in fixed positions while one of the portions is rotated in an oscillating manner while measuring load forces exerted by the shaft at one or more points of the shaft. Over time, a profile can be generated of the torsional fatigue life of the shaft, for example, the ability of the shaft to withstand torque at a given acceleration and/or a given angular displacement over time. In some embodiments, the testers and methods provided are safe and quiet to use, can be performed quickly, and can be used in an automated fashion without human supervision.

Figure 18:
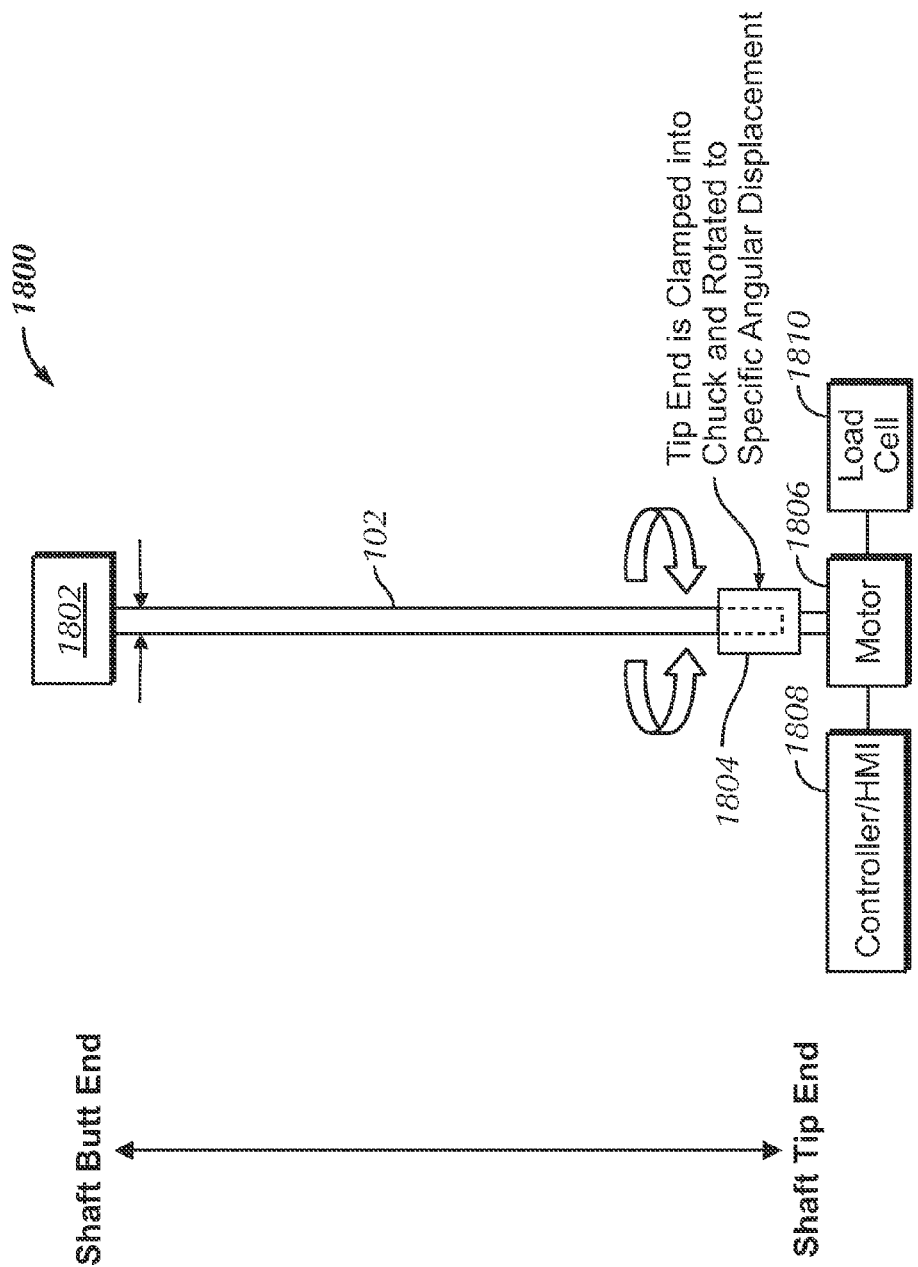
FIG. 18 is a free body diagram of torsional fatigue shaft testing device in accordance with further embodiments of the invention.

Referring next to FIG. 18, a free body diagram of a torsional fatigue device 1800 is shown in accordance with some embodiments of the present invention. FIG. 18 depicts a shaft 102 having a butt end and a tip end, the butt end held by a clamp 1802, the shaft tip end held by a chuck 1804, the chuck being rotatable and coupled to a motor 1806, the motor adapted to apply a rotational force to the chuck. A controller 1808 or human-machine interface (HMI) is coupled to the motor. A load cell (not shown) is also coupled to the motor.

In operation, the shaft butt end is loaded into a clamp 1802. In some embodiments, the shaft butt end is loaded into a lathe chuck, block or other device to fixedly hold a shaft. The clamp is tightened so as to hold the shaft butt end in a fixed position. In some embodiments, the clamp is manually tightened. In some embodiments, the clamp is automatically tightened. In some embodiments, during operation, the shaft butt end that is fixedly held does not rotate within the clamp or move in any of the X, Y or Z-directions.

The shaft tip end is loaded into a chuck 1806 and locked in place. In some embodiments, the shaft tip end is loaded into a clamp, block or other device to fixedly hold a shaft. The chuck is tightened so as to hold the shaft tip end in a fixed position. In some embodiments, the chuck is manually tightened. In some embodiments, the chuck 1804 is automatically tightened. In some embodiments, during operation, the shaft tip end that is fixedly held does not rotate within the clamp or move in any of the X, Y or Z-directions. In some embodiments, the chuck fits about the shaft tip end about to the same extent that a hosel of a golf club head covers a golf shaft.

It is noted that the clamp 1802 and the chuck 1804 that hold the shaft butt end and shaft tip end, respectively, may be generically referred to as a holder or support that holds or supports a portion (e.g., the shaft butt end, or shaft tip end) of the shaft. In some embodiments, the chuck of is bi-directionally rotatable. That is, the chuck is adapted to rotate both clockwise and counterclockwise. When the shaft tip end is locked, or otherwise fixedly held in the chuck, rotation of the chuck introduces a rotational or an angular displacement of the shaft tip end relative to the shaft butt end.

Still referring to FIG. 18, a motor 1806 (e.g., a rotary motor) is shown that is adapted to introduce a rotational force on the chuck. In operation, the motor rotates the chuck which, in turn, introduces an angular displacement on the shaft tip end that is fixedly held in the chuck. The motor controls partial rotations of the chuck. The motor also has the capability to be easily manipulated or programmed for automatic operation using a controller/HMI and can run for extended periods of time under nominal loads. In some embodiments, the motor includes a rotary encoder in order to determine (and output) its circumferential location at all points in time.

In some embodiments, the torsional fatigue machine includes one or more load cells. In some embodiments, the load cell is coupled to the motor and measures the stress on the shaft due to the angular displacement of a first portion of the shaft relative to a second portion of the shaft. In some embodiments, the load cell is coupled to the shaft 102. An amplifier (not shown, but similar to amplifier 220) is used to increase the signal output by the load cell. The load applied to a shaft, and measured by the load cell, is dependent upon many factors including the thickness and strength of the shaft, the amount of angular displacement and the acceleration at which the angular displacement occurs.

In some embodiments, a frame (not shown) supports the various features of the torsional fatigue machine. In some embodiments, the frame is made of aluminum for its structural members. It is understood that the frame may comprise one or more frames or one or more frame members or other structure to support the various components herein described. In some embodiments, the frame is generally rectangular. The height of the frame may be adjusted to accommodate shafts of various sizes. In some embodiments, the frame supports the chuck, clamp and motor.

When a shaft is secured at both ends and the machine is in operation, the motor 1806 rotates the chuck 1804 causing an angular displacement in the shaft tip end relative to the shaft butt end. In some embodiments, the amount of angular displacement introduced by the motor is determined at least in part using a measured amount of angular displacement of a golf shaft as measured during a golf swing. In this manner, the fatigue tester machine mimics the force applied and/or moment generated at a golf shaft when it is in use. According to some embodiments and using data gathered from measurements and/or input by the user, an angular displacement is determined that enables the torsional fatigue strength of the shaft to be tested. The motor 1806 rotates the chuck from an equilibrium position to a first angular displacement with an acceleration profile. The motor then returns to the equilibrium position from the first angular displacement and proceeds in the direction of angular momentum, i.e., in the opposite direction of the first angular displacement, to a second angular displacement at the same acceleration profile. In several embodiments, the first and second positions of angular displacement are of the same magnitude, but are on opposite sides the equilibrium position. The motor continues to rotate the chuck, and thus the shaft tip end, from the first to the second angular displacements, and vice versa, through the equilibrium. In preferred embodiments, the motor does not rotate the chuck 360 degrees. In this manner, according to several embodiments, the chuck, by virtue of the motor, introduces a bidirectional oscillating angular displacement to the shaft.

The acceleration profile or the acceleration of the motor's oscillations are input into the controller/HMI. Similar parameters as those described herein, such as with reference to FIGS. 12 and 13 may be used. In this manner, the fatigue tester machine mimics the force applied to a golf shaft or the moment generated by a golf shaft when it is in use since the acceleration profile of a shaft under test is similar to the acceleration of angular displacement experienced by a golf shaft when in use. The torsional fatigue strength of the shaft can be determined using data gathered from measurements of a shaft that is oscillating with an acceleration profile in accordance with this description.

In some embodiments, a user initiates testing by interacting with a human machine interface (HMI) or other computer. In some embodiments, a user initiates testing by interacting with a PC coupled to the system (i.e., a controller/HMI includes a personal computer). In some embodiments, the system runs until manually terminated. In alternative embodiments, the system is automatically terminated when failure occurs (a shaft breaks) or a stopping event occurs. A stopping event is, for example, an elapse of a user-selected amount of time, a change in load, or other event in response to which the testing will terminate.

While the machine is running, the load measurements and corresponding rotary location measurements or readings are output to a controller to be stored and/or processed (or further output to a computer). Load cell measurements are correlated to circumferential positions measured by the encoder in order to output, display, and/or process load measurements. In some embodiments, the user can program the frequency at which to record and/or display load measurements.

The torsional fatigue testers described herein may be used with a variety of different shafts, such as sports implements (e.g., golf shafts, pole vault shafts, baseball bats, etc.) or any other shaft that is intended to experience torsional fatigue. Over a period of testing, torsional fatigue characteristics can be generated from load measurements to determine the torsional endurance of a shaft, for example, for quality control purposes.

In some embodiments, data from a load cell is sent to a PC (not shown) and a representation of the data displayed. Data relating to the load at one or more points on the shaft is sent to the PC. Data relating to the number of oscillations of the shaft is sent to the PC. In some embodiments, fatigue life of a shaft may be predicted based upon data gathered at the PC.

This specification describes several shaft testing devices and related methods. In one embodiment, a shaft test comprises a frame, a first shaft support coupled to the frame, the first shaft support adapted to support a first portion of a shaft at a first fixed position, and a second shaft support coupled to the frame, the second shaft support adapted to support a second portion of the shaft. The second shaft support is adapted to introduce a displacement of the second portion of the shaft relative to the first portion of the shaft. In one variation, the second shaft support holder is adapted to laterally move the second portion of the shaft relative to the first portion to introduce a lateral displacement to the shaft. In another variation, the shaft tester further comprises a third shaft support coupled to a third portion of the shaft, the third portion in between the first portion and the second portion, the third support adapted to support the third portion at a second fixed position such that the shaft bends about the third portion when the second shaft support laterally moves the second portion of the shaft relative to the first portion. In another variation, the shaft tester further comprises a linear bearing guide coupling the second shaft support to the frame and adapted such that the second shaft support can be fixed at a plurality of locations along the linear bearing guide. Additionally, the shaft tester comprises a motor coupled to the shaft and adapted to rotate the shaft while laterally displaced. In a further variation, the first shaft support is adapted to allow the shaft to rotate when the shaft is experiencing the lateral displacement. In another variation, the first shaft support and the second shaft support are adapted to allow the shaft to rotate 360 degrees when the shaft is experiencing the lateral displacement. In another variation, the shaft tester further comprises an encoder adapted to measure an angular position of the shaft. In a further variation, the second shaft support fits about the second portion of the shaft about to the same extent that a hosel of a golf club head covers a golf shaft. I yet another variation, a load cell is coupled to the second shaft support for measuring a force due to the displacement of the shaft.

In another embodiment, a method for testing a shaft comprises the steps: holding a first portion of a shaft; holding a second portion of the shaft; and displacing the second portion of the shaft relative to the first portion. In a variation, the displacing step comprises laterally displacing the second portion of the shaft relative to the first portion. In a further variation, the displacing step comprises displacing the second portion of the shaft relative to the first portion and about a first support at a third portion of the shaft, the third portion in between the first portion and the second portion, the first support adapted to maintain a fixed position such that the shaft bends about the third portion. In another variation, the method also comprises rotating the shaft while maintaining the displacement. In another variation, the method also measures a load exerted by the second portion while displacing and rotating the shaft. In a further variation, the method includes generating a profile of the load over time while displacing and rotating the shaft. In another variation, the method further measures a load exerted by the second portion while displacing the shaft. And in another variation, the method generates a profile of the load over time while displacing the shaft.

In a further embodiment, a shaft tester comprises a frame, a first holder coupled to the frame, the first holder adapted to hold a first portion of a shaft and a second holder coupled to the frame, the second holder adapted to hold a second portion of the shaft. The second holder is adapted to introduce an angular displacement of the second portion of the shaft relative to the first portion of the shaft. In one variation, the angular displacement is introduced by a motor coupled to the second holder. In another variation, the tester includes an encoder coupled to the motor and adapted to measure the angular displacement of the shaft. In a further variation, the tester includes a load cell coupled to the motor and adapted to measure a force due to the angular displacement of the shaft. In another variation, the second holder is a rotatable chuck. In a further variation, the second holder fits about the second portion of the shaft about to the same extent that a hosel of a golf club head covers a golf shaft. In another variation, the second holder is adapted to allow a bidirectional oscillating angular displacement of the second portion of the shaft relative to the first portion of the shaft.

In a further embodiment, a method for testing a shaft comprising the steps: holding a first portion of a shaft; holding a second portion of the shaft; and angularly displacing the second portion of the shaft relative to the first portion. In one variation, the step of angularly displacing is accomplished at least in part by a motor. In another variation, the method measures with an encoder the angular displacement of the shaft. In another variation, the method measures with a load cell a force due to the angular displacement of the shaft. In a further variation, the step of holding a second portion of the shaft is accomplished at least in part by a rotatable chuck. In another variation, the step of holding a second portion of the shaft comprises fitting a holder about the second portion of the shaft about to the same extent that a hosel of a golf club head covers a golf shaft. And in another variation, the step of angularly displacing comprises allowing a bidirectional oscillating angular displacement of the second portion of the shaft relative to the first portion of the shaft.

While the invention herein disclosed has been described by means of specific embodiments, examples and applications thereof, numerous modifications and variations could be made thereto by those skilled in the art.

What is claimed is:

1. A shaft tester comprising:
   a frame;
   a first shaft support coupled to the frame, the first shaft support adapted to support a first portion of a shaft at a first fixed position;
   a second shaft support coupled to the frame, the second shaft support adapted to support a second portion of the shaft at a second fixed position;
   a third shaft support coupled to the frame, the third shaft support adapted to support a third portion of the shaft at a third fixed position;
   an actuator coupled to the third shaft support and adapted to displace the third portion relative to the first portion and the second portion to cause a deflection in the shaft;
   a sensor coupled to one of the first support, the second support and the third support and adapted to output a signal corresponding to a load force exerted by the shaft due to the deflection;
   a controller coupled to the actuator and adapted to control displacement of the shaft; and
   a computer adapted to generate a fatigue profile of the shaft based at least in part on the load force exerted by the shaft due to the deflection over time.

2. The shaft tester of claim 1 further comprising a motor adapted to rotate the shaft when the shaft experiences the deflection.

3. The shaft tester of claim 2 wherein the controller is adapted to control one or more of a speed of rotation of the shaft, a time duration of the rotation, an acceleration of the rotation, and a number of cycles of the rotation.

4. The shaft tester of claim 2 wherein the first shaft support, the second shaft support and the third shaft support are adapted to allow the shaft to rotate 360 degrees when the shaft experiences the deflection.

5. The shaft tester of claim 1 wherein the controller is adapted to control one or more of an amount of the deflection, a force caused by the deflection, and a time duration of the deflection.

6. A shaft tester comprising:
   a frame;
   a first shaft support coupled to the frame, the first shaft support adapted to support a first portion of a shaft at a first fixed position;
   a second shaft support coupled to the frame, the second shaft support adapted to support a second portion of the shaft at a second fixed position;

a third shaft support coupled to the frame, the third shaft support adapted to support a third portion of the shaft at a third fixed position;
an actuator coupled to the third shaft support and adapted to displace the third portion relative to the first portion and the second portion to cause a deflection in the shaft;
a sensor coupled to one of the first support, the second support and the third support and adapted to output a signal corresponding to a load force exerted by the shaft due to the deflection; and
a controller coupled to the actuator and adapted to control displacement of the shaft;
wherein the actuator is adapted to displace the third portion with enough force to break the shaft.

7. The shaft tester of claim 1 wherein the first portion is proximate a butt end of the shaft, the third portion is at a tip end, and the second is in between the first portion and second portion.

8. The shaft tester of claim 7 wherein the third shaft support fits about the tip end of the shaft about to a same extent that a hosel of a golf club head covers a golf shaft.

9. The shaft tester of claim 1 wherein the sensor comprises a load cell.

10. The shaft tester of claim 1 wherein the actuator adapted to laterally displace the third portion relative to the first portion and the second portion to cause a lateral deflection in the shaft.

11. The shaft tester of claim 1 wherein the computer is coupled to the controller.

12. A shaft tester comprising:
a frame;
a first shaft support coupled to the frame, the first shaft support adapted to support a first portion of a shaft at a first fixed position;
a second shaft support coupled to the frame, the second shaft support adapted to support a second portion of the shaft at a second fixed position;
an actuator coupled to the second shaft support and adapted to displace the second portion relative to the first portion to cause a lateral deflection in the shaft;
a sensor coupled to one of the first support and the second support and adapted to output a signal corresponding to a load force exerted by the shaft due to the lateral deflection;
a motor adapted to rotate the shaft when the shaft experiences the lateral deflection;
a controller coupled to the actuator and the motor and adapted to control the deflection and rotation; and
a computer adapted to generate a fatigue profile of the shaft based at least in part on the load force exerted by the shaft due to the deflection over time.

13. The shaft tester of claim 12 wherein the controller is adapted to control one or more of an amount of a speed of the rotation of the shaft, a time duration of the rotation, an acceleration of the rotation, and a number of cycles of the rotation.

14. The shaft tester of claim 12 wherein the first shaft support and the second shaft support are adapted to allow the shaft to rotate 360 degrees when the shaft is experiencing the lateral deflection.

15. A method for use in testing a shaft comprising:
supporting a first portion of a shaft at a first fixed position;
supporting a second portion of a shaft at a second fixed position;
supporting a third portion of a shaft at a third fixed position;
displacing the third portion relative to the first portion and the second portion causing a deflection in the shaft;
outputting a signal corresponding to a load force exerted by the shaft due to the displacing;
controlling a displacement of the shaft; and
generating a fatigue profile based at least in part on signals output.

16. The method of claim 15 further comprising rotating the shaft when the shaft experiences the deflection.

17. The method of claim 16 wherein the controlling step comprises controlling one or more of a speed of rotation of the shaft, a time duration of the rotation, an acceleration of the rotation, and a number of cycles of the rotation.

18. The method of claim 16 further comprising allowing the shaft to rotate 360 degrees during the rotating step and while the shaft experiences the deflection.

19. The method of claim 16 wherein the rotating comprising rotating the shaft when the shaft experiences the deflection until the shaft fails.

20. The method of claim 15 wherein the controlling step comprises controlling one or more of an amount of the deflection, a force caused by the deflection, and a time duration of the deflection.

21. A method for use in testing a shaft comprising:
supporting a first portion of a shaft at a first fixed position;
supporting a second portion of a shaft at a second fixed position;
supporting a third portion of a shaft at a third fixed position;
displacing the third portion relative to the first portion and the second portion causing a deflection in the shaft;
outputting a signal corresponding to a load force exerted by the shaft due to the displacing;
controlling a displacement of the shaft; and
wherein the displacing step comprises displacing the third portion with enough force to break the shaft.

22. The method of claim 15 wherein the first portion is proximate a butt end of the shaft, the third portion is at a tip end, and the second is in between the first portion and second portion.

23. The method of claim 22 wherein the third portion is supported about to a same extent that a hosel of a golf club head covers and supports a golf shaft.

24. The method of claim 15 wherein the displacing step comprises laterally displacing the third portion relative to the first portion and the second portion causing a lateral deflection in the shaft.

25. The method of claim 15 further comprising measuring the load force.

26. A method for use in testing a shaft comprising:
supporting a first portion of a shaft at a first fixed position;
supporting a second portion of a shaft at a second fixed position;
laterally displacing the second portion relative to the first portion and the second portion causing a lateral deflection in the shaft;
outputting a signal corresponding to a load force exerted by the shaft due to the displacing;
rotating the shaft during the displacing step;
controlling the displacing and the rotating of the shaft; and
generating a fatigue profile based at least in part on signals output.

27. The method of claim 26 wherein the controlling step comprises controlling one or more of an amount of a speed of the rotation of the shaft, a time duration of the rotation, an acceleration of the rotation, and a number of cycles of the rotation.

28. The method of claim 26 wherein the rotating step comprises rotating the shaft over 360 degrees.

29. A method for use in testing a shaft comprising:

displacing a first portion of a shaft relative to a second portion of the shaft to cause a deflection in the shaft;

rotating the shaft when the shaft is experiencing the deflection;

measuring a load force exerted by the shaft due to the deflection during the rotation;

monitoring the measured load force over time; and generating a fatigue profile of the shaft based at least in part on the monitoring step.

30. A method for use in testing a shaft comprising:

displacing a first portion of a first shaft relative to a second portion of the first shaft to cause a deflection in the first shaft causing a load force at a first level to be exerted by the first shaft;

rotating the first shaft when the first shaft is experiencing the deflection until the first shaft fails;

determining a first length of time until the first shaft failed;

displacing a first portion of a second shaft relative to a second portion of the second shaft to cause a deflection in the second shaft causing a load force at a second level to be exerted by the second shaft;

rotating the second shaft when the second shaft is experiencing the deflection until the second shaft fails;

determining a second length of time until the second shaft failed; and generating a fatigue life profile based at least in part on testing the first shaft and the second to extrapolate a fatigue life of additional shafts not tested.

* * * * *